United States Patent
Mayorga et al.

(10) Patent No.: US 9,627,193 B2
(45) Date of Patent: Apr. 18, 2017

(54) ORGANOAMINODISILANE PRECURSORS AND METHODS FOR DEPOSITING FILMS COMPRISING SAME

(71) Applicant: AIR PRODUCTS AND CHEMICALS, INC., Allentown, PA (US)

(72) Inventors: Steven Gerard Mayorga, Oceanside, CA (US); Heather Regina Bowen, Vista, CA (US); Xinjian Lei, Vista, PA (US); Manchao Xiao, San Diego, CA (US); Haripin Chandra, Vista, CA (US); Anupama Mallikarjunan, San Marcos, CA (US); Ronald Martin Pearlstein, San Marcos, CA (US)

(73) Assignee: VERSUM MATERIALS US, LLC, Allentown, PA (US)

( * ) Notice: Subject to any disclaimer, the term of this patent is extended or adjusted under 35 U.S.C. 154(b) by 94 days.

(21) Appl. No.: 14/511,719

(22) Filed: Oct. 10, 2014

(65) Prior Publication Data
US 2015/0024608 A1 Jan. 22, 2015

Related U.S. Application Data

(63) Continuation of application No. 13/902,300, filed on May 24, 2013, now Pat. No. 9,337,018.

(60) Provisional application No. 61/654,508, filed on Jun. 1, 2012.

(51) Int. Cl.
| | |
|---|---|
| C07F 7/02 | (2006.01) |
| H01L 21/02 | (2006.01) |
| C09D 1/00 | (2006.01) |
| C07F 7/10 | (2006.01) |
| C23C 16/18 | (2006.01) |
| C23C 16/40 | (2006.01) |
| C23C 16/455 | (2006.01) |
| C23C 16/46 | (2006.01) |

(52) U.S. Cl.
CPC ........ *H01L 21/02219* (2013.01); *C07F 7/025* (2013.01); *C07F 7/10* (2013.01); *C09D 1/00* (2013.01); *C23C 16/18* (2013.01); *C23C 16/401* (2013.01); *C23C 16/45542* (2013.01); *C23C 16/46* (2013.01); *H01L 21/0217* (2013.01); *H01L 21/0228* (2013.01); *H01L 21/0262* (2013.01); *H01L 21/02164* (2013.01); *H01L 21/02167* (2013.01); *H01L 21/02271* (2013.01); *H01L 21/02532* (2013.01); *Y10T 428/13* (2015.01)

(58) Field of Classification Search
CPC .............................. C07F 7/025; C23C 16/345
USPC ....... 556/407, 410; 548/406; 546/14; 544/69
See application file for complete search history.

(56) References Cited

U.S. PATENT DOCUMENTS

| | | |
|---|---|---|
| 5,660,895 A | 8/1997 | Lee et al. |
| 6,837,251 B1 | 1/2005 | Zorich et al. |
| 7,019,159 B2 | 3/2006 | Dussarrat et al. |
| 7,064,083 B2 | 6/2006 | Dussarrat et al. |
| 7,077,904 B2 | 7/2006 | Cho et al. |
| 7,446,217 B2 | 11/2008 | Wang et al. |

(Continued)

FOREIGN PATENT DOCUMENTS

| | | |
|---|---|---|
| CN | 1356181 | 7/2002 |
| CN | 102295657 | 4/2015 |

(Continued)

OTHER PUBLICATIONS

H. Schuh, et al, Disilanyl-amines—Compounds Comprising the Structural Unit Si—Si—N, as Single-Source Precursors for Plasma-Enhanced Chemical Vapour Deposition (PE-CVD) of Silicon Nitride, Z. anorg. allg. Chem, 1993, 1347-1352.

M. Abedini, et al, The Preparation and Properties of Some New Nitrogen and Fluorine Derivatives of Disilane, Inorganic Chemistry, 1963, 608-613.

(Continued)

*Primary Examiner* — Porfirio Nazario Gonzalez
(74) *Attorney, Agent, or Firm* — Michael K. Boyer

(57) ABSTRACT

Described herein are precursors and methods for forming silicon-containing films. In one aspect, there is provided a precursor of Formula I:

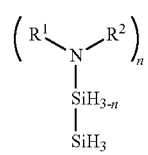

wherein $R^1$ is selected from linear or branched $C_3$ to $C_{10}$ alkyl group, linear or branched $C_3$ to $C_{10}$ alkenyl group, linear or branched $C_3$ to $C_{10}$ alkynyl group, $C_1$ to $C_6$ dialkylamino group, electron withdrawing group, and $C_6$ to $C_{10}$ aryl group; $R^2$ is selected from hydrogen, linear or branched $C_1$ to $C_{10}$ alkyl group, linear or branched $C_3$ to $C_6$ alkenyl group, linear or branched $C_3$ to $C_6$ alkynyl group, $C_1$ to $C_6$ dialkylamino group, $C_6$ to $C_{10}$ aryl group, linear or branched $C_1$ to $C_6$ fluorinated alkyl group, electron withdrawing group, and $C_4$ to $C_{10}$ aryl group; optionally wherein $R^1$ and $R^2$ are linked together to form ring selected from substituted or unsubstituted aromatic ring or substituted or unsubstituted aliphatic ring; and n=1 or 2.

20 Claims, 4 Drawing Sheets

(56) References Cited

U.S. PATENT DOCUMENTS

| | | |
|---|---|---|
| 7,531,679 B2 | 5/2009 | Wang et al. |
| 7,713,346 B2 | 5/2010 | Wang et al. |
| 7,786,320 B2 | 8/2010 | Wang et al. |
| 7,887,883 B2 | 2/2011 | Wang et al. |
| 7,910,765 B2 | 3/2011 | Wang et al. |
| 8,153,832 B2 | 4/2012 | Dussarrat |
| 8,753,984 B2 | 6/2014 | Murakami et al. |
| 8,912,353 B2 | 12/2014 | Xiao et al. |
| 8,946,065 B2 | 2/2015 | Okada et al. |
| 2002/0184945 A1 | 12/2002 | Chase et al. |
| 2005/0037627 A1 | 2/2005 | Dussarrat et al. |
| 2006/0269667 A1 | 11/2006 | Ma et al. |
| 2008/0058541 A1 | 3/2008 | Bowen et al. |
| 2009/0209081 A1 | 8/2009 | Matero et al. |
| 2010/0016620 A1 | 1/2010 | Dussarrat |
| 2013/0109155 A1 | 5/2013 | Okada et al. |
| 2013/0109197 A1 | 5/2013 | Murakami et al. |
| 2014/0187024 A1 | 7/2014 | Obu et al. |
| 2015/0037970 A1 | 2/2015 | Hasebe et al. |
| 2015/0094470 A1 | 4/2015 | Sanchez et al. |

FOREIGN PATENT DOCUMENTS

| | | |
|---|---|---|
| JP | 08277292 | 10/1996 |
| JP | 11147889 | 6/1999 |
| JP | 2000195801 | 7/2000 |
| JP | 2003075234 | 3/2003 |
| JP | 2003168683 | 6/2003 |
| JP | 2006096675 | 4/2006 |
| JP | 2006517517 A | 7/2006 |
| JP | 2006310865 | 11/2006 |
| JP | 2007509836 | 4/2007 |
| JP | 2008074847 | 4/2008 |
| WO | 2004044958 A2 | 5/2004 |
| WO | 2005045899 A2 | 5/2005 |
| WO | 2006036538 A2 | 4/2006 |
| WO | 2006091264 A1 | 8/2006 |
| WO | 2006138131 A1 | 12/2006 |
| WO | 2007112779 | 10/2007 |
| WO | 2009006272 A1 | 1/2009 |

OTHER PUBLICATIONS

M. Soldner, et al, 1,2-Disilanediyl Bis(triflate), F3CSO3-SiH2SiH2-O3SCF3, as the Key Intermediate for a Facile Preparation of Open-Chain and Cycli 1,1- and 1,2-Diaminodisilanes, Inorg. Chem, 1997, 1758-1763.

STN Registry, CAS RN 22140-71-2, Nov. 16, 1984.

ORGANOAMINODISILANE PRECURSORS AND METHODS FOR DEPOSITING FILMS COMPRISING SAME

CROSS-REFERENCE OF RELATED APPLICATIONS

This application is a continuation-in-part of U.S. patent application Ser. No. 13/902,300, filed on May 24, 2013, which in turn claims the benefit of priority under 35 U.S.C. §119(e) to U.S. provisional application Ser. No. 61/654,508, filed Jun. 1, 2012, which is incorporated herein by reference in its entirety.

BACKGROUND OF THE INVENTION

Precursors, particularly organoaminodisilane, and compositions thereof that can be used for the deposition of silicon-containing films, including but not limited to, silicon amorphous silicon, crystalline silicon, silicon nitride, silicon oxide, carbon doped silicon oxide, silicon carbo-nitride, and silicon oxynitride films are described herein. In yet another aspect, described herein is the use of the organoaminodisilane precursors for depositing silicon-containing films in the fabrication of integrated circuit devices. In these or other aspects, the organoaminodisilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Several classes of compounds can be used as precursors for silicon-containing films such as, but not limited to, silicon oxide, carbon doped silicon oxide or silicon nitride films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Low pressure chemical vapor deposition (LPCVD) processes are one of the more widely accepted methods used by semiconductor industry for the deposition of silicon-containing films. Low pressure chemical vapor deposition (LP-CVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Precursors that are used in depositing silicon nitride films such as BTBAS and chlorosilanes generally deposit the films at temperatures greater than 550° C. The trend of miniaturization of semiconductor devices and low thermal budget requires lower process temperature and higher deposition rate. The temperature, at which the silicon films are deposited, should decrease in order to prevent ion diffusion in the lattice, particularly for those substrates comprising metallization layers and on many Group III-V and II-VI devices. Accordingly, there is a need in the art to provide precursors for the deposition of silicon-containing films, such as silicon oxide, carbon doped silicon oxide, silicon oxynitride, or silicon nitride films that are sufficiently chemically reactive to allow deposition via CVD, ALD or other processes at temperatures of 550° C. or below or even at room temperature.

The reference entitled "Disilanyl-amines—Compounds Comprising the Structure Unit Si—Si—N, as Single-Source Precursors for Plasma-Enhanced Chemical Vapor Deposition (PE-CVD) of Silicon Nitride", Schuh et al., Zeitschrift Für Anorganische and Allgemeine Chemie, 619 (1993), pp. 1347-52 describes potential single-source precursors for PECVD of silicon nitride films wherein the precursors have the structural unit Si—Si—N such as $(Et_2N)_2HSi-SiH_3$, $(Et_2N)_2HSi-SiH(NEt_2)_2[(i-Pr)_2N]H_2Si-SiH_3$ and $[(i-Pr)_2N]H_2Si-SiH_2[N(i-Pr)_2]$. The precursor 1,2-bis(di-i-propylamino)disilane (BIPADS) was used for the PECVD deposition of silicon nitride films. The resulting films from the BIPADS precursor exhibited refractive indices ranging from 1.631-1.814 and had low carbon and very low oxygen contents but high (Si-bound) hydrogen contents.

The reference entitled "1,2-Disilanediyl Bis(triflate), $F_3CSO_3-SiH_2-SiH_2-O_3SCF_3$, as the Key Intermediate for a Facile Preparation of Open-Chain and Cyclic 1,1- and 1,2-Diaminodisilanes", Sölder et al., Inorganic Chemistry, 36 (1997), pp. 1758-63 describes high yield syntheses for several open-chain and cyclic diaminodisilanes with fully hydrogenated Si linkages.

U.S. Pat. No. 5,660,895 describes the deposition of high-quality $SiO_2$ films at low temperatures in a PECVD process using disilane $(Si_2H_6)$ and nitrous oxide.

U.S. Pat. Nos. 7,019,159 and 7,064,083 describe a composition and method of preparing silane compounds or hexakis(monohydrocarbylamino)disilanes that are free of chlorine and have the formula: $((R)HN)_3-Si-Si-(NH(R))_3$ wherein R independently represents a $C_1$ to $C_4$ hydrocarbyl. The hexakis(monohydrocarbylamino)disilane precursors are used for the deposition of silicon nitride or silicon oxynitride films.

U.S. Pat. No. 8,153,832 describes pentakis(dimethylamino)disilane compounds having the formula: $Si_2(NMe_2)_5Y$ where Y is selected from the group consisting of H, Cl, or an amino group and its use for manufacturing gate silicon-containing films or etch-stop silicon-containing films of SiN or SiON.

US Publ. No. 2009/0209081 A describes methods for depositing silicon dioxide containing thin films on a substrate using hexakis(monoalkylamino)disilane such as hexakis(ethylamino)disilane as silicon source and ozone as oxidant. The growth rate was about 1.1 Å/cycle.

U.S. Pat. No. 7,077,904 describes methods for depositing silicon dioxide containing thin films on a substrate using hexachlorodisilane as silicon source and water as oxidant in presence of catalyst such as pyridine. The growth rates were in the range from 2.6 to 0.6 Å/cycle at substrate temperatures from 50 to 140° C.

US Publ. No. 2013/0109155 describes a method of forming a seed layer for a thin film using an aminosilane based gas having two Si atoms such as hexakisethylaminodisilane $(C_{12}H_{36}N_6Si_2)$. Other aminosilanes having the following formulas may also be used: (1) (R1R2)N)nSi2H6-n-m(R3)m . . . n: the number of amino groups, m: the number of alkyl groups or (2) (R1)NH)nSi2H6-n-m(R3)m . . . n: the number of amino groups, m: the number of alkyl groups. In formulas (1) and (2), R1, R2, R3=CH₃, C₂H₅, C₃H₇, R1=R2=R3 or may not be the same as each other, n=an integer ranging from 1 to 6 and m=0, and 1 to 5.

U.S. Pat. Nos. 7,446,217; 7,531,679; 7,713,346; 7,786,320; 7,887,883; and 7,910,765 describe silane precursors that comprise at least one disilane derivative that is fully substituted with alkylamino and/or dialkylamino functional groups. Besides the foregoing, there have been a few mono-dialkylaminodisilanes reported in the art such as dimethylaminodisilane (CAS #14396-26-0P), diethylaminodisilane (CAS #132905-0-5), and di-iso-propylaminodisilane (CAS #151625-25-1).

BRIEF SUMMARY OF THE INVENTION

Described herein are organoaminodisilane precursors having a Si—N bond, a Si—Si bond and a Si—H₃ group, compositions comprising same, and methods using same for forming films comprising silicon, such as, but not limited to, amorphous silicon, crystalline silicon, silicon oxide, carbon doped silicon oxide, silicon nitride, silicon oxynitride, silicon carbide, silicon carbonitride, and combinations thereof onto at least a portion of a substrate. In addition, described herein is a composition comprising an organoaminodisilane described herein wherein the organoaminodisilane is substantially free of at least one selected from the amines, halides, higher molecular weight species, and trace metals. In these or other embodiments, the composition may further comprise a solvent. Also disclosed herein are the methods to form films comprising silicon or coatings on an object to be processed, such as, for example, a semiconductor wafer. In one embodiment of the method described herein, a film comprising silicon and oxygen is deposited onto a substrate using an organoaminodisilane precursor and an oxygen-containing source in a deposition chamber under conditions for generating a silicon oxide, carbon doped silicon oxide film on the substrate. In another embodiment of the method described herein, a film comprising silicon and nitrogen is deposited onto a substrate using an organoaminodisilane precursor and a nitrogen containing precursor in a deposition chamber under conditions for generating a silicon nitride film on the substrate. In a further embodiment, the organoaminodisilane precursors described herein can also be used a dopant for metal containing films, such as but not limited to, metal oxide films or metal nitride films. In the compositions and methods described herein, an organoaminodisilane having the formula described herein is employed as at least one of the silicon containing precursors.

In one aspect, the organoaminodisilane precursor described herein comprises at least one organoaminodisilane precursor comprising a Si—N bond, a Si—Si bond, and a Si—H₃ group represented by the following Formula I below:

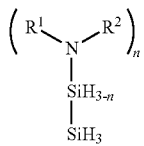

wherein R¹ is selected from a linear or branched C₃ to C₁₀ alkyl group, a linear or branched C₃ to C₁₀ alkenyl group, a linear or branched C₃ to C₁₀ alkynyl group, a C₁ to C₆ dialkylamino group, an electron withdrawing group, and a C₆ to C₁₀ aryl group; R² is selected from hydrogen, a linear or branched C₁ to C₁₀ alkyl group, a linear or branched C₃ to C₆ alkenyl group, a linear or branched C₃ to C₆ alkynyl group, a C₁ to C₆ dialkylamino group, a C₆ to C₁₀ aryl group, a linear or branched C₁ to C₆ fluorinated alkyl group, an electron withdrawing group, and a C₄ to C₁₀ aryl group; optionally wherein R¹ and R² are linked together to form a ring selected from a substituted or unsubstituted aromatic ring or a substituted or unsubstituted aliphatic ring; and n=1 or 2. In certain embodiments of Formula I, R¹ and R² are linked together to form a ring. In one particular embodiment, R¹ and R² are selected from a linear or a branched C₃ to C₆ alkyl group and are linked to form a cyclic ring. In alternative embodiments of Formula I, R¹ and R² are not linked together to form a ring. In certain embodiments of Formula I, R¹ and R² are the same with the proviso that they cannot both be iso-propyl. In other embodiments, R¹ and R² are different.

In another aspect, there is provided a composition comprising: (a) at least one organoaminodisilane precursor comprising a Si—N bond, a Si—Si bond, and a Si—H₃ group represented by the following Formula I below:

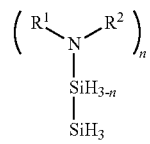

wherein R¹ is selected from a linear or branched C₃ to C₁₀ alkyl group, a linear or branched C₃ to C₁₀ alkenyl group, a linear or branched C₃ to C₁₀ alkynyl group, a C₁ to C₆ dialkylamino group, an electron withdrawing group, and a C₆ to C₁₀ aryl group; R² is selected from hydrogen, a linear or branched C₁ to C₁₀ alkyl group, a linear or branched C₃ to C₆ alkenyl group, a linear or branched C₃ to C₆ alkynyl group, a C₁ to C₆ dialkylamino group, a C₆ to C₁₀ aryl group, a linear or branched C₁ to C₆ fluorinated alkyl group, an electron withdrawing group, and a C₄ to C₁₀ aryl group; optionally wherein R¹ and R² are linked together to form a ring selected from a substituted or unsubstituted aromatic ring or a substituted or unsubstituted aliphatic ring; and n=1 or 2; and (b) a solvent. In certain embodiments of the composition described herein, exemplary solvents can include, without limitation, ether, tertiary amine, alkyl hydrocarbon, aromatic hydrocarbon, tertiary aminoether, and combinations thereof. In certain embodiments, the difference between the boiling point of the organoaminodisilane and the boiling point of the solvent is 40° C. or less.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using at least one organoaminodisilane precursor comprising a Si—N bond, a Si—Si bond, and a Si—H₃ group represented by the following Formula I below:

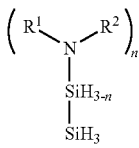

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2. In certain embodiments, $R^1$ and $R^2$ are the same. In other embodiments, $R^1$ and $R^2$ are different. In the foregoing or other embodiments, $R^1$ and $R^2$ can be linked together to form a ring. In further embodiments, $R^1$ and $R^2$ are not linked together to form a ring.

In another aspect, there is provided a method of forming a silicon oxide, carbon doped silicon oxide film via an atomic layer deposition process or ALD-like process, the method comprising the steps of:
  a. providing a substrate in a reactor;
  b. introducing into the reactor at least one organoaminodisilane precursor comprising a Si—N bond, a Si—Si bond, and a Si—H$_3$ group represented by the following Formula I below:

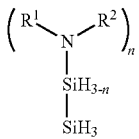

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;
  c. purging the reactor with a purge gas;
  d. introducing an oxygen-containing source into the reactor; and
  e. purging the reactor with a purge gas; wherein steps b through e are repeated until a desired thickness of the film is obtained. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring In a further aspect, there is provided a method of forming a film selected from a silicon oxide film and a carbon doped silicon oxide film onto at least a surface of a substrate using a CVD process comprising:
  a. providing a substrate in a reactor;
  b. introducing into the reactor at least one organoaminodisilane precursor comprising a Si—N bond, a Si—Si bond, and a Si—H$_3$ group represented by the following Formula I below:

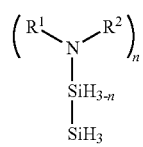

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2; and
  c. providing an oxygen-containing source to deposit the film onto the at least one surface. In certain embodiments of the method, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In another aspect, there is provided a method of forming a silicon nitride film via an atomic layer deposition process, the method comprising the steps of:
  a. providing a substrate in a reactor;
  b. introducing into the reactor an at least one organoaminodisilane precursor comprising a Si—N bond, a Si—Si bond, and a Si—H$_3$ group represented by the following Formula I below:

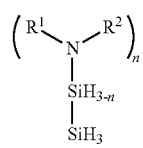

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;

c. purging the reactor with a purge gas;
   d. introducing a nitrogen-containing source into the reactor;
   e. purging the reactor with a purge gas; and wherein steps b through e are repeated until a desired thickness of the silicon nitride film is obtained. In certain embodiments, $R^1$ and $R^2$ in Formula I are the same. In other embodiments, $R^1$ and $R^2$ are different. In the foregoing or other embodiments, $R^1$ and $R^2$ can be linked together to form a ring. In a further embodiment, $R^1$ and $R^2$ are not linked together to form a ring.

In a further aspect, there is provided a method of forming a silicon nitride film onto at least a surface of a substrate using a CVD process comprising:
   a. providing a substrate in a reactor;
   b. introducing into the reactor at least one organoaminodisilane precursor comprising a Si—N bond, a Si—Si bond, and a Si—$H_3$ group represented by the following Formula I below:

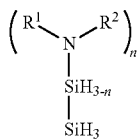

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;

c. providing a nitrogen-containing source wherein the at least one organoaminodisilane precursors and the nitrogen-containing source react to deposit the film onto the at least one surface. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In a further embodiment of the method described herein, the process is depositing an amorphous or a crystalline silicon film. In this embodiment, the method comprises:
   placing one or more substrates into a reactor which is heated to one or more temperatures ranging from ambient temperature to about 700° C.;
   introducing at least one organoaminodisilane precursor comprising a Si—N bond, a Si—Si bond, and a Si—$H_3$ group represented by the following Formula I below:

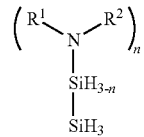

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2; and
   providing a reducing agent source into the reactor to at least partially react with the at least one organoaminodisilane precursor and deposit a silicon-containing film onto the one or more substrates. The reducing agent is selected from the group consisting of hydrogen, hydrogen plasma, and hydrogen chloride. In certain embodiments of the CVD method, the reactor is maintained at a pressure ranging from 10 mTorr to 760 Torr during the introducing step. The above steps define one cycle for the method described herein, and the cycle of steps can be repeated until the desired thickness of a film is obtained. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring.

In another aspect, there is provided a method of depositing an amorphous or a crystalline silicon film via an atomic layer deposition or cyclic chemical vapor deposition process, the method comprising the steps of:
   a. providing a substrate in a reactor;
   b. introducing into the reactor at least one organoaminodisilane precursor comprising a Si—N bond, a Si—Si bond, and a Si—$H_3$ group represented by the following Formula I below:

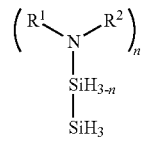

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2 wherein step b is repeated until a desired thickness of the film is obtained. In certain embodiments, the thickness of the film can be 1 Å or greater, or 1 to 10,000 Å, or 1 to 1000 Å, or 1 to 100 Å.

In another aspect, a vessel for depositing a silicon-containing film comprising one or more organoaminodisilane precursor having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process.

In another aspect, there is provided a composition comprising an organoaminodisilane represented by the structure of Formula I:

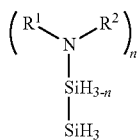

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2 wherein the composition is substantially free of halide ions. In one particular embodiment, the composition comprises an organoaminodisilane having Formula I wherein $R^1$ and $R^2$ are both iso-propyl groups.

DETAILED DESCRIPTION OF THE INVENTION

Figure 1:
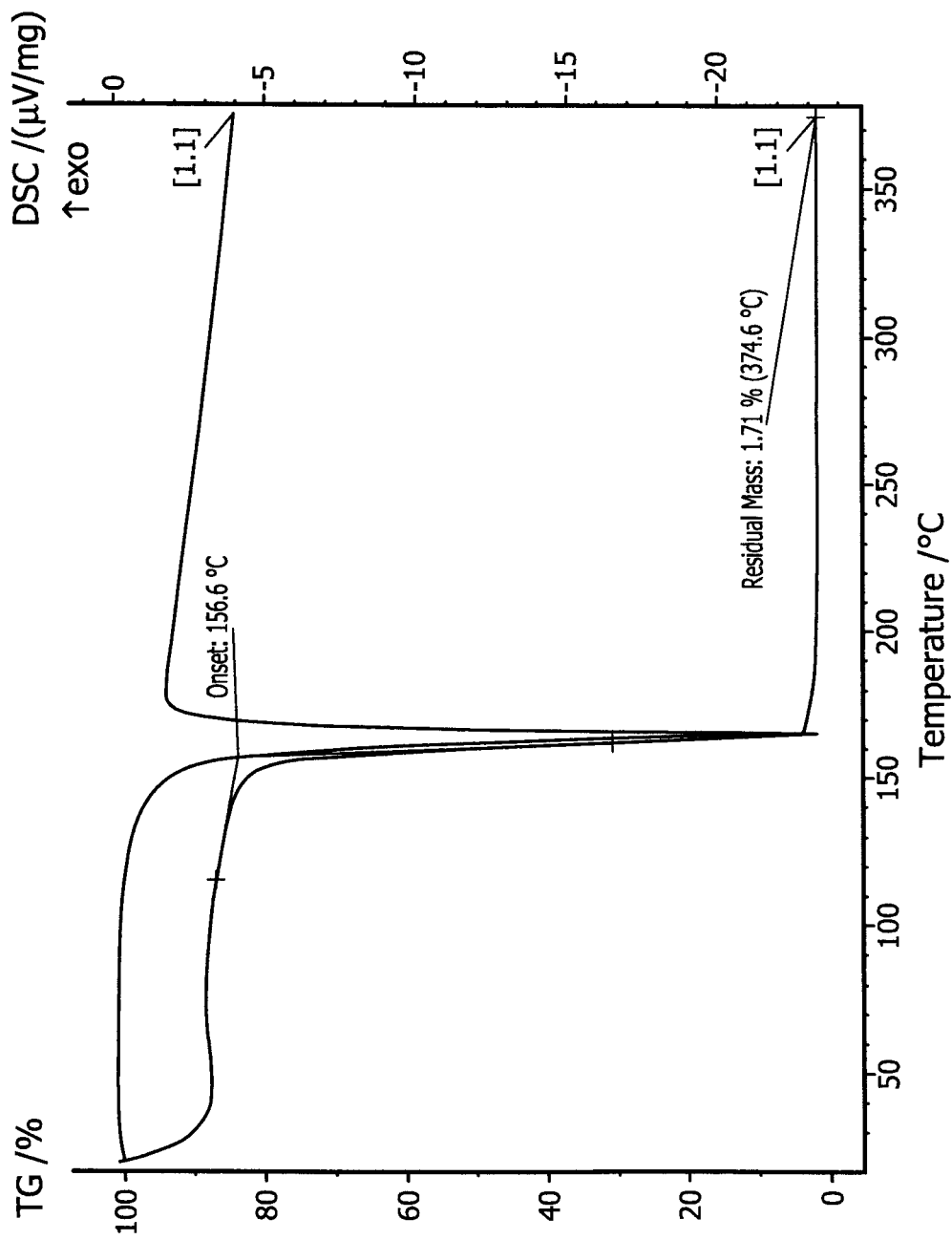
FIG. 1 shows the TGA/DSC graph of di-iso-propylaminodisilane, wherein the TGA demonstrates that the compound is volatile and the DSC shows it has a boiling point of about 157° C.

The organoaminodisilanes described herein are used as precursors to form stoichiometric and non-stoichiometric silicon containing films such as, but not limited to, amorphous silicon, crystalline silicon, silicon oxide, silicon oxycarbide, silicon nitride, silicon oxynitride, and silicon oxycarbonitride. These precursors can also be used, for example, as dopants for metal containing films. The organoaminodisilane precursors used in semi-conductor processes are typically high purity volatile liquid precursor chemical that are vaporized and delivered to a deposition chamber or reactor as a gas to deposit a silicon containing film via CVD or ALD processes for semiconductor devices. The selection of precursor materials for deposition depends upon the desired resultant silicon-containing material or film. For example, a precursor material may be chosen for its content of chemical elements, its stoichiometric ratios of the chemical elements, and/or the resultant silicon containing film or coating that are formed under CVD. The precursor material may also be chosen for various other characteristics such as cost, relatively low toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

The organoaminodisilane precursors described herein exhibit a balance of reactivity and stability that makes them ideally suitable as CVD or ALD precursors in microelectronic device manufacturing processes. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor under a given vacuum to prevent condensation or particles from forming in the container, lines, or both. With regard to stability, other precursors may form silane ($SiH_4$) or disilane ($Si_2H_6$) as they degrade. Silane is pyrophoric at room temperature or it can spontaneously combust which presents safety and handling issues. Moreover, the formation of silane or disilane and other by-products decreases the purity level of the precursor and changes as small as 1-2% in chemical purity may be considered unacceptable for reliable semiconductor manufacture. In certain embodiments, the organoaminodisilane precursors having Formula I described herein comprise 2% or less by weight, or 1% or less by weight, or 0.5% or less by weight of by-product (such as the corresponding bis-disilane byproduct) after being stored for a time period of 6 months or greater, or one year or greater which is indicative of being shelf stable. In addition to the foregoing advantages, in certain embodiments, such as for depositing a silicon oxide or silicon nitride or silicon film using an ALD, ALD-like, PEALD, or CCVD deposition method, the organoaminodisilane precursor described herein may be able to deposit high density materials at relatively low deposition temperatures, e.g., 500° C. or less, or 400° C. or less, 300° C. or less, 200° C. or less, 100° C. or less, or 50° C. or less. In one particular embodiment, the organoaminodisilane precursor, such as di-iso-propylaminodisilane or di-sec-butylaminodisilane or 2,6-dimethylpiperidinodisilane can be used to deposit a silicon-containing film via ALD or PEALD at a temperature as low as 50° C. or less or at ambient or room temperature (e.g., 25° C.).

Without being bound by theory, it is believed that Formula I precursors can generate $H_2Si$: di-radicals or $H_3Si$ radical upon heating which can promote formation oligomers containing Si—Si bonds or anchor on the surface of a substrate.

In certain embodiments, these oligomers or anchored SiH$_2$ or SiH$_3$ can further form amorphous silicon films. In this or other embodiments, those oligomers function as a seed layer for subsequent deposition of silicon or silicon oxide films.

In one embodiment, described herein is a composition for forming a silicon-containing film comprising: an organoaminodisilane having Formula I described herein and a solvent(s). Without being bound by any theory, it is believed that composition described herein may provide one or more advantages compared to pure organoaminodisilane. These advantages include: better usage of the organoaminodisilane in semiconductor processes, better stability over long term storage, cleaner evaporation by flash vaporization, and/or overall more stable direct liquid injection (DLI) chemical vapor deposition process. The weight percentage of the organoaminodisilane in the composition can range from 1 to 99% with the balance being solvent(s) wherein the solvent(s) does not react with the organoaminodisilane and has a boiling point similar to the organoaminodisilane. With regard to the latter, the difference between the boiling points of the organoaminodisilane and solvent(s) in the composition is 40° C. or less, more preferably 20° C. or less, or 10° C. or less. Exemplary compositions include, but not limited to, a mixture of di-iso-propylaminodisilane (b.p. about 157° C.) and octane (b.p. 125 to 126° C.), a mixture of di-iso-propylaminodisilane (b.p. about 157° C.) and ethylcyclohexane (b.p. 130-132° C.), di-iso-propylaminodisilane (b.p. about 157° C.) and toluene (b.p. 115° C.), a mixture of di-sec-butylaminodisilane and decane (b.p. 174° C.), a mixture of di-sec-butylaminodisilane and decane, and a mixture of di-sec-butylaminodisilane and 2,2'-oxybis(N,N-dimethylethanamine (b.p., 189° C.).

In one aspect, there is provided at least one organoaminodisilane precursor comprising a Si—N bond, a Si—Si bond, and a Si—H$_3$ group represented by the following Formula I below:

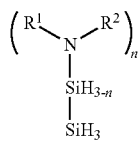

wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, a linear or branched C$_1$ to C$_6$ fluorinated alkyl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring; and n=1 or 2. Further in embodiments wherein n=2, any one or all of R$^1$ and R$^1$, R$^1$ and R$^2$, or R$^2$ and R$^2$ can be linked to form a ring. In certain embodiments of Formula I, R$^1$ and R$^2$ are the same with the proviso that they cannot both be iso-propyl. In other embodiments, R$^1$ and R$^2$ are different. In one embodiment, R$^1$ and R$^2$ are selected from a linear or branched C$_3$ to C$_6$ alkyl group and are linked to form a cyclic ring. In the yet further embodiments, R$^1$ and R$^2$ are not linked together to form a ring.

For the organoaminodisilane precursors of Formula A wherein n=1, the organoaminodisilane precursor has the following Formula IA wherein R$^1$ and R$^2$ are as described herein and are optionally linked to form a ring structure.

Formula IA

The organoaminodisilane precursors of Formula A wherein n=2, the organoaminodisilane precursor has the following Formula IB wherein R' is equivalent to R$^2$ defined aforementioned and R$^1$ and R$^2$ are as described herein and are optionally linked to form a ring structure:

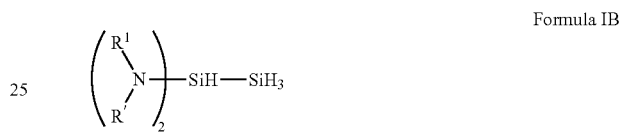

Formula IB

In the formulae and throughout the description, the term "alkyl" denotes a linear, or branched functional group having from 1 to 10 or 1 to 6 carbon atoms. Exemplary alkyl groups include, but are not limited to, methyl, ethyl, propyl, isopropyl, butyl, isobutyl, sec-butyl, tert-butyl, pentyl, isopentyl, tert-pentyl, hexyl, iso-hexyl, and neo-hexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In the formulae and throughout the description, the term "cyclic alkyl" denotes a cyclic functional group having from 3 to 10 or from 4 to 10 carbon atoms or from 5 to 10 carbon atoms. Exemplary cyclic alkyl groups include, but are not limited to, cyclobutyl, cyclopentyl, cyclohexyl, and cyclooctyl groups.

In the formulae and throughout the description, the term "aryl" denotes an aromatic cyclic functional group having from 5 to 12 carbon atoms or from 6 to 10 carbon atoms. Exemplary aryl groups include, but are not limited to, phenyl, benzyl, chlorobenzyl, tolyl, and o-xylyl.

In the formulae and throughout the description, the term "alkenyl group" denotes a group which has one or more carbon-carbon double bonds and has from 3 to 10 or from 3 to 6 or from 3 to 4 carbon atoms.

In the formulae and throughout the description, the term "alkynyl group" denotes a group which has one or more carbon-carbon triple bonds and has from 3 to 10 or from 3 to 6 or from 3 to 4 carbon atoms.

In the formulae and throughout the description, the term "alkoxy" denotes an alkyl group which has is linked to an oxygen atom (e.g., R—O) and may have from 1 to 10, or from 1 to 6, or from 1 to 4 carbon atoms. Exemplary alkoxy groups include, but are not limited to, methoxy (—OCH$_3$), ethoxy(—OCH$_2$CH$_3$), n-propoxy (—OCH$_2$CH$_2$CH$_3$), and iso-propoxy (—OCHMe$_2$).

In the formulae and throughout the description, the term "dialkylamino group" denotes a group which has two alkyl groups attached to a nitrogen atom and has from 1 to 10 or from 2 to 6 or from 2 to 4 carbon atoms.

The term "electron withdrawing group" as used herein describes an atom or group thereof that acts to draw electrons away from the Si—N bond. Examples of suitable electron withdrawing groups or substituents include, but are not limited to, nitriles (CN). In certain embodiments, electron withdrawing substituent can be adjacent to or proximal to N in any one of Formula I. Further non-limiting examples of an electron withdrawing group includes F, Cl, Br, I, CN, $NO_2$, RSO, and/or $RSO_2$ wherein R can be a $C_1$ to $C_{10}$ alkyl group such as, but not limited to, a methyl group or another group.

In certain embodiments, one or more of the alkyl group, alkenyl group, alkynyl group, alkoxy group, dialkylamino group, aryl group, and/or electron withdrawing group in Formula I may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxy group, dialkylamino aryl group, and/or electron withdrawing group in Formula I may be unsubstituted.

In certain embodiments, $R^1$ is selected from a $C_1$ to $C_{10}$ alkyl group, preferably a branched $C_3$ to $C_6$ alkyl group such as iso-propyl, sec-butyl, tert-butyl, tert-pentyl (amyl) whereas $R^2$ is hydrogen and n=2. Exemplary of these particular embodiments include, but are not limited to:

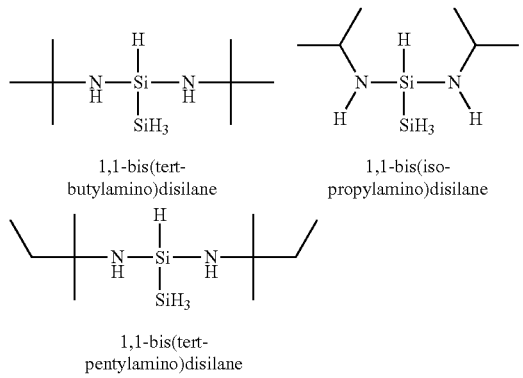

1,1-bis(tert-butylamino)disilane 1,1-bis(iso-propylamino)disilane 1,1-bis(tert-pentylamino)disilane In certain embodiments, $R^1$ and $R^2$ are linked in Formula I to form a ring structure. In these embodiments, $R^2$ is not hydrogen. For example, in an embodiment where $R^1$ and $R^2$ are linked together to form a ring, $R^2$ may include a bond (instead of a hydrogen substituent) for linking to $R^1$. Thus, in this particular embodiment, $R^2$ may be selected from for example, a $C_1$ to $C_{10}$ alkyl moiety, a $C_3$ to $C_{10}$ alkenyl moiety or a linear or branched $C_3$ to $C_{10}$ alkynyl moiety. In these or other embodiments, the ring structure can be unsaturated such as, for example, a cyclic alkyl ring, or saturated, for example, an aryl ring. Further, in these or other embodiments, the ring structure can also be substituted or substituted. In one particular embodiment, the organoaminodisilane comprises an aliphatic, substituted ring such as a heteroatomic cyclic functional group having from 5 to 10 carbon atoms and at least one nitrogen atom. Exemplary of these particular embodiments include, but are not limited to, 1,2-bis(pyrrolidino)disilane wherein $R^1$=propyl and $R^2$=Me, 1,2-bis(piperidino)disilane wherein $R^1$=propyl and $R^2$=Et, 2,6-dimethylpiperidinodisilane wherein $R^1$=iso-propyl and $R^2$=sec-butyl, and 2,5-dimethylpyrrolidinodilane wherein $R^1$=$R^2$=iso-propyl.

In certain embodiments of Formula I, $R^1$ is selected from a $C_3$ to $C_{10}$ alkyl group, preferably a branched $C_3$ to $C_6$ alkyl group such as iso-propyl, sec-butyl, tert-butyl, tert-pentyl (amyl) whereas $R^2$ is selected from a $C_1$ to $C_{10}$ alkyl group, preferably $C_1$ to $C_6$ alkyl group, and n=2. Exemplary of these particular embodiments include, but are not limited to:

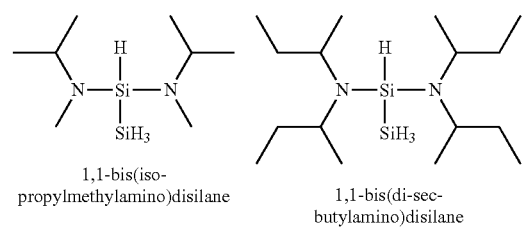

1,1-bis(iso-propylmethylamino)disilane 1,1-bis(di-sec-butylamino)disilane

In one particular embodiment of Formula I, n=2 and $R^1$ and $R^1$ are linked to form an aliphatic ring which can further be substituted or unsubstituted. Exemplary structures of these embodiments of Formula I are shown below:

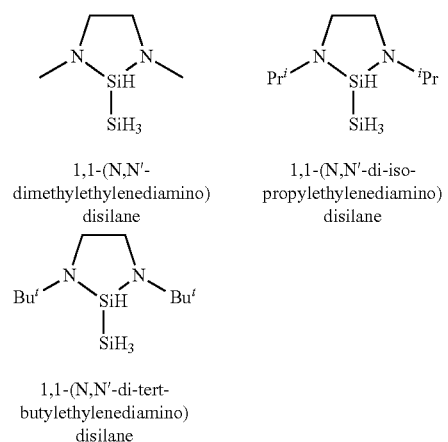

1,1-(N,N'-dimethylethylenediamino) disilane 1,1-(N,N'-di-iso-propylethylenediamino) disilane 1,1-(N,N'-di-tert-butylethylenediamino) disilane In another particular embodiment of Formula I, n=2 and $R^1$ and $R^2$ are linked to form an aliphatic ring which can further be substituted or unsubstituted. Exemplary structures of these embodiments of Formula I are shown below:

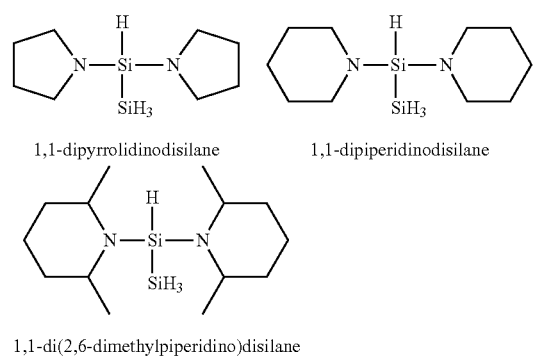

1,1-dipyrrolidinodisilane 1,1-dipiperidinodisilane 1,1-di(2,6-dimethylpiperidino)disilane In other embodiments, $R^1$ and $R^2$ are not linked in Formula I.

In certain embodiments, the at least one organoaminodisilane precursor having Formula I has one or more substituents comprising oxygen or nitrogen atoms. In this or other embodiments, substituents $R^1$ and $R^2$ are linked via an oxygen or a nitrogen atom in Formula I to form a ring structure.

Without being bound by theory, it is believed that organoaminodisilane precursors such as those organoaminodisilanes having Formula I described herein comprising a Si—N bond, a Si—Si bond and a SiH$_3$ group are advantageous over known organoaminodisilane precursors containing only Si—N and Si—Si bonds or only Si—Cl and Si—Si bonds. In this regard, it is believed that the organoaminodisilanes described herein having four or five Si—H groups, one —Si—N bond and one Si—Si bond make them more reactive than other organoaminodisilane precursors, allowing deposition temperatures to be lower than other known organoaminodisilanes, such as, for example, hexachlorodisilane. It is believed that the unique structures of the Formula 1 precursors described herein allow for deposition temperatures of 400° C. or less, 300° C. or less, 200° C. or less, 100° C. or less, or 25° C.

In certain embodiments, the organoaminodisilanes having Formula I can be prepared by reacting a monochlorodisilane (MCDS) or monobromodisilane (MBDS) or lower molecular dialkylaminodisilane such as di-iso-propylaminodisilane or di-sec-butylaminodisilane with an amine having the following Formula II in an organic solvent or solvent mixture.

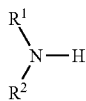

II

In Formula II, $R^1$ and $R^2$ are the same as in the substituents described in Formula I. The following Equation 1 provide a non-limiting example of a reaction schemes or synthesis route which may be used to make the organoaminodisilanes having Formula I as described herein. The reaction in Equation (1) can be conducted with (e.g., in the presence of) or without (e.g., in the absence of) organic solvents. In embodiments wherein an organic solvent is used, examples of suitable organic solvents include, but are not limited to, hydrocarbon such as hexanes, octane, toluene, and ethers such as diethylether and tetrahydrofuran (THF). In these or other embodiments, the reaction temperature is in the range of from about −70° C. to the boiling point of the solvent employed if a solvent is used. The resulting organoaminodisilane can be purified, for example, via vacuum distillation after removing all by-products as well as any solvent(s) if present.

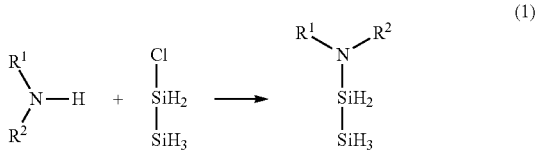

(1)

Equation 1 is one synthetic route to make the organoaminodisilanes having Formula I involving a reaction between monohalidodisilane (XSiH$_2$SiH$_3$ wherein X═Cl, Br, I) and a secondary amine presented in Formula II. Other synthetic routes may be also employed to make these organoaminodisilanes as disclosed in the prior art, for example reducing monoaminochlorodisilanes with metal hydride or disproportionation of monoaminocholordisilane or reacting disilane with secondary amine in presence of catalyst.

The organoaminodisilane precursors according to the present invention and compositions comprising the organoaminodisilane precursors according to the present invention are preferably substantially free of halide ions. As used herein, the term "substantially free" as it relates to halide ions (or halides) such as, for example, chlorides and fluorides, bromides, and iodides, means less than 5 ppm (by weight), preferably less than 3 ppm, and more preferably less than 1 ppm, and most preferably 0 ppm. Chlorides are known to act as decomposition catalysts for organoaminodisilanes. Significant levels of chloride in the final product can cause the organoaminodisilane precursor to degrade. The gradual degradation of the organoaminodisilane may directly impact the film deposition process making it difficult for the semiconductor manufacturer to meet film specifications. In addition, the shelf-life or stability is negatively impacted by the higher degradation rate of the organoaminodisilane thereby making it difficult to guarantee a 1-2 year shelf-life. Moreover, organoaminodisilanes are known to form flammable and/or pyrophoric gases upon decomposition such as hydrogen and silane. Therefore, the accelerated decomposition of the organoaminodisilane presents safety and performance concerns related to the formation of these flammable and/or pyrophoric gaseous byproducts.

Compositions according to the present invention that are substantially free of halides can be achieved by (1) reducing or eliminating chloride sources during chemical synthesis, and/or (2) implementing an effective purification process to remove chloride from the crude product such that the final purified product is substantially free of chlorides. Chloride sources may be reduced during synthesis by using reagents that do not contain halides such as chlorodislanes, bromodisilanes, or iododislanes thereby avoiding the production of by-products that contain halide ions. In addition, the aforementioned reagents should be substantially free of chloride impurities such that the resulting crude product is substantially free of chloride impurities. In a similar manner, the synthesis should not use halide based solvents, catalysts, or solvents which contain unacceptably high levels of halide contamination. The crude product may also be treated by various purification methods to render the final product substantially free of halides such as chlorides. Such methods are well described in the prior art and, may include, but are not limited to, purification processes such as distillation, or adsorption. Distillation is commonly used to separate impurities from the desire product by exploiting differences in boiling point. Adsorption may also be used to take advantage of the differential adsorptive properties of the components to effect separation such that the final product is substantially free of halide. Adsorbents such as, for example, commercially available MgO—Al$_2$O$_3$ blends can be used to remove halides such as chloride.

The method used to form the silicon-containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon-containing film is deposited using an ALD process. In another embodiment, the silicon-containing film is deposited using a CCVD process. In a further embodiment, the silicon-containing film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the silicon-containing film. In one embodiment, the film is deposited via an ALD process by exposing the substrate surface alternatively to the one or more the silicon-containing precursor, oxygen-containing source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors other than the organoaminodisilane precursor having the above Formula I. Examples of additional silicon-containing precursors include, but are not limited to, mono-aminosilane (e.g., di-iso-propylaminosilane, di-sec-butylaminosilane, phenylmethylaminosilane; organo-silicon compounds such as trisilylamine (TSA); monoaminosilane (di-iso-propylaminosilane, di-sec-butylaminosilane, phenylmethylaminosilane); siloxanes (e.g., hexamethyl disiloxane (HMDSO) and dimethyl siloxane (DMSO)); organosilanes (e.g., methylsilane, dimethylsilane, diethylsilane, vinyl trimethylsilane, trimethylsilane, tetramethylsilane, ethylsilane, disilylmethane, 2,4-disilapentane, 1,4-disilabutane, 2,5-disilahexane, 2,2-disilylpropane, 1,3,5-trisilacyclohexane and fluorinated derivatives of these compounds); phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or organoaminodisilane precursor may be introduced into the reactor for a predetermined time period. In certain embodiments, the time period ranges from about 0.001 to about 500 seconds.

In certain embodiments, the silicon-containing films deposited using the methods described herein are formed in the presence of oxygen using an oxygen-containing source, reagent or precursor comprising oxygen. An oxygen-containing source may be introduced into the reactor in the form of at least one oxygen-containing source and/or may be present incidentally in the other precursors used in the deposition process. Suitable oxygen-containing source gases may include, for example, water ($H_2O$) (e.g., deionized water, purifier water, and/or distilled water), oxygen ($O_2$), oxygen plasma, ozone ($O_3$), NO, $N_2O$, $NO_2$, carbon monoxide (CO), carbon dioxide ($CO_2$) and combinations thereof. In certain embodiments, the oxygen-containing source comprises an oxygen-containing source gas that is introduced into the reactor at a flow rate ranging from about 1 to about 2000 square cubic centimeters (sccm) or from about 1 to about 1000 sccm. The oxygen-containing source can be introduced for a time that ranges from about 0.1 to about 100 seconds. In one particular embodiment, the oxygen-containing source comprises water having a temperature of 10° C. or greater. In embodiments wherein the film is deposited by an ALD or a cyclic CVD process, the precursor pulse can have a pulse duration that is greater than 0.01 seconds, and the oxygen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen-containing source or reagent is provided in a molecular amount less than a 1:1 ratio to the silicon precursor, so that at least some carbon is retained in the as deposited silicon-containing film.

In certain embodiments, the silicon-containing films comprise silicon and nitrogen. In these embodiments, the silicon-containing films deposited using the methods described herein are formed in the presence of nitrogen-containing source. A nitrogen-containing source may be introduced into the reactor in the form of at least one nitrogen-containing source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen-containing source, the nitrogen-containing source, and/or other precursors, source gases, and/or reagents may be performed by changing the time for supplying them to change the stoichiometric composition of the resulting silicon-containing film.

Energy is applied to the at least one of the precursor, nitrogen-containing source, reducing agent, other precursors or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminodisilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the precursor(s) having Formula I is used in a composition comprising a solvent and an organoaminodisilane precursor having Formula I described herein, the solvent or mixture thereof selected does not react with the organoaminodisilane. The amount of solvent by weight percentage in the composition ranges from 0.5% by weight to 99.5% or from 10% by weight to 75%. In this or other embodiments, the solvent has a boiling point (b.p.) similar to the b.p. of the organoaminodisilane of Formula I or the difference between the b.p. of the solvent and the b.p. of the organoaminosilane of Formula I is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof. Some non-limiting exemplary compositions include, but not limited to, a composition comprising di-iso-propylaminodisilane (b.p. about 157° C.) and octane (b.p. 125 to 126° C.); a composition comprising di-iso-propylaminodisilane (b.p. about 157° C.) and ethylcyclohexane (b.p. 130-132° C.); a composition comprising di-iso-propylaminodisilane (b.p. about 157° C.) and toluene (b.p. 115° C.); a composition comprising di-sec-butylaminodisilane and decane (b.p. 174° C.); and a composition comprising di-sec-butylaminodisilane and 2,2'-oxybis(N,N-dimethylethanamine) (b.p., 189° C.).

In another embodiment, a vessel for depositing a silicon-containing film comprising one or more organoaminodisilane precursor having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the organoaminodisilane precursor having Formula I is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the organoaminodisilane precursor and/or other precursor can be maintained in separate vessels or in a single vessel having separation means for maintaining the organoaminodisilane precursor and other precursor separate during storage.

In one embodiment of the method described herein, a cyclic deposition process such as CCVD, ALD, or PEALD may be employed, wherein at least one silicon-containing precursor selected from an organoaminodisilane precursor having the formula described herein and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments, the gas lines connecting from the precursor canisters to the reaction chamber are heated to one or more temperatures depending upon the process requirements and the container of the organoaminodisilane precursor having the formula I described herein is kept at one or more temperatures for bubbling. In other embodiments, a solution comprising the at least one silicon-containing precursor having the formula described herein is injected into a vaporizer kept at one or more temperatures for direct liquid injection.

A flow of argon and/or other gas may be employed as a carrier gas to help deliver the vapor of the at least one organoaminodisilane precursor to the reaction chamber during the precursor pulsing. In certain embodiments, the reaction chamber process pressure is about 1 Torr.

In a typical ALD or CCVD process, a substrate such as, without limitation, a silicon oxide, carbon doped silicon oxide, flexible substrate, or metal nitride substrate is heated on a heater stage in a reaction chamber that is exposed to the silicon-containing precursor initially to allow the organoaminodisilane to chemically adsorb onto the surface of the substrate. A purge gas such as nitrogen, argon, or other inert gas purges away unabsorbed excess organoaminodisilane from the process chamber. After sufficient purging, an oxygen-containing source may be introduced into reaction chamber to react with the absorbed surface followed by another gas purge to remove reaction by-products from the chamber. The process cycle can be repeated to achieve the desired film thickness. In other embodiments, pumping under vacuum can be used to remove unabsorbed excess organoaminodisilane from the process chamber, after sufficient evacuation under pumping, an oxygen-containing source may be introduced into reaction chamber to react with the absorbed surface followed by another pumping down purge to remove reaction by-products from the chamber. In yet another embodiment, the organoaminodisilane and the oxygen-containing source can be co-flowed into reaction chamber to react on the substrate surface to deposit silicon oxide, carbon doped silicon oxide. In a certain embodiment of cyclic CVD, the purge step is not used.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon-containing film.

In another embodiment of the method disclosed herein, the films containing both silicon and nitrogen are formed using an ALD, PEALD, CCVD or PECCVD deposition method that comprises the steps of:
 a. providing a substrate in an ALD reactor;
 b. introducing into the ALD reactor at least one organoaminodisilane precursor comprising a Si—N bond, a Si—Si bond, and a Si—H$_3$ group represented by the following Formula I below:

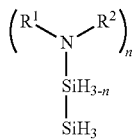

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;
 c. chemisorbing the at least one organoaminodisilane precursor onto a substrate;
 d. purging away the unreacted at least one organoaminodisilane precursor using a purge gas;
 e. providing a nitrogen-containing source to the organoaminodisilane precursor onto the heated substrate to react with the sorbed at least one organoaminodisilane precursor; and
 f. optionally purging or pumping away any unreacted nitrogen-containing source.

In another aspect, there is provided a method of forming a film selected from a silicon oxide and a carbon doped silicon oxide film via a PEALD or a PECCVD deposition process, the method comprising the steps of:
 a. providing a substrate in a reactor;
 b. introducing into the reactor oxygen along with at least one organoaminodisilane precursor comprising a Si—N bond, a Si—Si bond, and a Si—H$_3$ group represented by the following Formula I below:

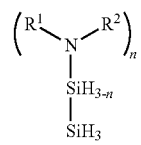

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;
 c. purging the reactor with a purge gas along with oxygen;
 d. applying RF plasma;
 e. purging the reactor with a purge gas or pumping the reactor to remove unreacted organoaminodisilane and any by-products; and wherein steps b through e are repeated until a desired thickness of the film is obtained.

In another embodiment of the method disclosed herein, the silicon-containing films is formed using a ALD deposition method that comprises the steps of:
 a. providing a substrate in a reactor;
 b. introducing into the reactor at least one organoaminodisilane precursor comprising a Si—N bond, a Si—Si bond, and a Si—H$_3$ group represented by the following Formula I below:

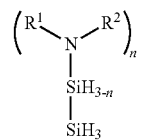

wherein R¹ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; R² is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein R¹ and R² are linked together to form a ring selected from a substituted or unsubstituted aromatic ring or a substituted or unsubstituted aliphatic ring; and n=1 or 2;

c. chemisorbing the at least one organoaminodisilane precursor onto a substrate;

d. purging away the unreacted at least one organoaminodisilane precursor using a purge gas;

e. providing an oxygen-containing source to the organoaminodisilane precursor onto the heated substrate to react with the sorbed at least one organoaminodisilane precursor; and f. optionally purging or pumping away any unreacted oxygen-containing source.

In another aspect, there is provided a method of forming a silicon nitride or silicon carbonitride film via PEALD or PECCVD process, the method comprising the steps of:

a. providing a substrate in a reactor;

b. introducing into the reactor a nitrogen-containing source and at least one organoaminodisilane precursor comprising a Si—N bond, a Si—Si bond, and a Si—H₃ group represented by the following Formula I below:

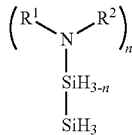

I wherein R¹ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; R² is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein R¹ and R² are linked together to form a ring selected from a substituted or unsubstituted aromatic ring or a substituted or unsubstituted aliphatic ring; and n=1 or 2;

c. purging the reactor with a purge gas along with the nitrogen-containing source;

d. applying RF plasma; and e. purging the reactor with a purge gas or pumping the reactor to remove unreacted organoaminodisilane and any by-products; and wherein steps b through e are repeated until a desired thickness of the film is obtained.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

For multi-component silicon-containing films, other precursors such as silicon-containing precursors, nitrogen-containing precursors, reducing agents, or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one organoaminodisilane precursor comprising a Si—N bond, a Si—Si bond, and a Si—H₃ group represented by the following Formula I below:

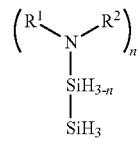

I wherein R¹ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; R² is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein R¹ and R² are linked together to form a ring selected from a substituted or unsubstituted aromatic ring or a substituted or unsubstituted aliphatic ring; and n=1 or 2; and c. providing an oxygen-containing source into the reactor to at least partially react with the at least one organoaminodisilane precursor and deposit a silicon-containing film onto the one or more substrates. In certain embodiments of the CVD method, the reactor is maintained at a pressure ranging from 10 mTorr to 760 Torr during the introducing step. The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

In a further embodiment of the method described herein, an amorphous or crystalline silicon film is deposited using the Formula I precursor described herein. In this embodiment, the method comprises:

a. placing one or more substrates into a reactor which is heated to a one or more temperatures ranging from ambient temperature to about 700° C.;

b. introducing at least one organoaminodisilane precursor comprising a Si—N bond, a Si—Si bond, and a Si—H₃ group represented by the following Formula I below:

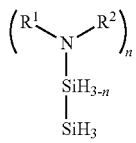

I wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2; and c. providing a reducing agent source into the reactor to at least partially react with the at least one organoaminodisilane precursor and deposit a silicon-containing film onto the one or more substrates. The reducing agent is selected from the group consisting of hydrogen, hydrogen plasma, hydrogen chloride. In certain embodiments of the CVD method, the reactor is maintained at a pressure ranging from 10 mTorr to 760 Torr during the introducing step. The above steps define one cycle for the method described herein; and the cycle can be repeated until the desired thickness of a film is obtained.

For multi-component silicon-containing films, other precursors such as silicon-containing precursors, nitrogen-containing precursors, oxygen-containing sources, reducing agents, and/or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one organoaminodisilane precursor comprising a Si—N bond, a Si—Si bond, and a Si—H₃ group represented by the following Formula I below:

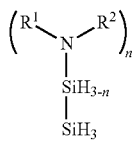

I wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2; and c. providing a nitrogen-containing source into the reactor to at least partially react with the at least one organoaminodisilane precursor and deposit a silicon-containing film onto the one or more substrates. In certain embodiments of the CVD method, the reactor is maintained at a pressure ranging from 10 mTorr to 760 Torr during the introducing step.

In a further embodiment of the method described herein, the organoaminodisilane precursors are used for depositing a silicon containing film which is an amorphous film, a crystalline silicon film, or a mixture thereof. In these embodiments, the silicon containing films is formed using a deposition method selected from ALD or cyclic CVD that comprises the steps of:

placing a substrates into a reactor which is heated to a temperature ranging from ambient temperature to about 700° C. and maintained at a pressure of 1 Torr or less;

introducing at least one organoaminodisilane precursor comprising a Si—N bond, a Si—Si bond, and a Si—H₃ group represented by the following Formula I below:

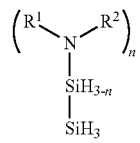

I wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and n=1 or 2;

providing a reducing agent into the reactor to at least partially react with the at least one organoaminosilane precursor and deposit a silicon containing film onto the one or more substrates wherein the reducing agent is at least one selected from the group consisting of hydrogen, hydrogen plasma, or hydrogen chloride. The above steps define one cycle for the method described herein; and the cycle can be repeated until the desired thickness of a silicon containing film is obtained. The desired thickness of the film can range from 1 Å to 10,000 Å.

In another aspect, there is provided a method of depositing amorphous or crystalline silicon film via an atomic layer deposition or cyclic chemical vapor deposition process or chemical vapor deposition at temperature lower than conventional silicon precursors, the method comprising the steps of:

a. providing a substrate in a reactor;
b. introducing into the reactor at least one organoaminodisilane precursor comprising a Si—N bond, a Si—Si bond, and a Si—H$_3$ group represented by the following Formula I below:

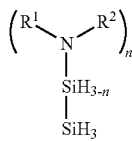

I wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, a linear or branched C$_1$ to C$_6$ fluorinated alkyl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring; and n=1 or 2;

c. purging the reactor with a purge gas wherein steps b through c are repeated until a desired thickness of the silicon film is obtained.

In a further embodiment of the method described herein, an silicon-containing film which may be amorphous or crystalline, and in one embodiment is a silicon carbonitride film, is deposited using the Formula I precursor described herein. In this embodiment, the method comprises:

a. placing one or more substrates into a reactor which is heated to a one or more temperatures ranging from ambient temperature to about 700° C.;
b. introducing at least one organoaminodisilane precursor represented by the following Formula I below:

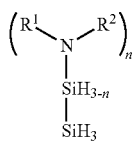

I wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, a linear or branched C$_1$ to C$_6$ fluorinated alkyl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring, and n=1 or 2; and c. purging the reactor with a purge gas;
d. providing a plasma source into the reactor to at least partially react with the at least one organoaminodisilane precursor and deposit a silicon-containing film onto the one or more substrates; and
e. purging the reactor with a purge gas.

In the method described above, steps b to e define one cycle and the cycle(s) can be repeated until the desired thickness of a film is obtained. The thickness of the film ranges from about 0.1 Å to about 1000 Å, or from about 0.1 Å to about 100 Å, or from about 0.1 Å to about 10 Å. The plasma source is selected from the group consisting of: a plasma comprising hydrogen and argon, a plasma comprising hydrogen and helium, an argon plasma, a helium plasma, other noble gas(es) (e.g., neon (Ne), krypton (Kr), and xenon (Xe)) plasma, and combinations thereof. In one particular embodiment of the method, the silicon-containing film comprises silicon carbonitride.

In certain embodiments, the organoaminodisilane precursors having Formula I described herein can also be used as a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the resultant silicon-containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon-containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon-containing film that is formed using the organoaminodisilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to 50%; and H ranges from about 0% to about 50% atomic percent weight % wherein x+y+z+v+w=100 atomic weight percent, as determined for example, by XPS or other means. Another example of the silicon containing film that is formed using the organoaminodisilane precursors and processes described herein is silicon carbonitride wherein the carbon content is from 1 at % to 80 at % measured by XPS. In yet, another example of the silicon containing film that is formed using the organoaminodisilane precursors and processes described herein is amorphous silicon wherein both sum of nitrogen and carbon contents is <10 at %, preferably <5 at %, most preferably <1 at % measured by XPS.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, a flexible substrate, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), light emitting diodes (LED), organic light emitting diodes (OLED), IGZO, and liquid crystal displays (LCD).

The following examples illustrate the method for preparing organoaminodisilane precursors as well as depositing silicon-containing films described herein and are not intended to limit it in any way.

EXAMPLES

In the following examples, unless stated otherwise, properties were obtained from sample films that were deposited onto medium resistivity (8-12 Ωcm) single crystal silicon wafer substrates.

Example 1

Synthesis of di-iso-propylaminodisilane (DIPADS) from Monochlorodisilane

In a 3-necked round bottom flask equipped with a mechanic stirrer, a condenser, and an addition funnel, a solution of 1 equivalent monochlorodisilane in hexane was cooled to −10° C. with a cold bath. With stirring, 2 equivalent of di-iso-propylamine was added dropwise through the addition funnel. After the addition was completed, the reaction mixture was allowed to warm up to room temperature. The reaction mixture was stirred at room temperature for 2 hours, followed by filtration. A distillation removed solvent hexane from the filtrate. The product di-iso-propylaminodisilane was obtained by vacuum distillation. Gas chromatography (GC) showed that it was >99% pure di-iso-propylaminodisilane (DIPADS) ($^1$H NMR (500 MHz, $C_7D_8$): δ=4.89 (m, $SiH_2$), 3.31 (t, $SiH_3$), 2.93 (m, $CHMe_2$), 1.00 (d, $CHMe_2$). FIG. 1 shows the TGA/DSC graph of di-iso-propylaminodisilane, wherein the TGA demonstrates that the compound is volatile and the DSC shows it has a boiling point of about 157° C.

Additional organoaminodisilane precursors of Formula I were made via exchange reaction between di-iso-propylaminodisilane with corresponding amines and were characterized by mass spectroscopy (MS). The molecular weight (MW), the structure, and corresponding MS fragmentation peaks of each organoaminosilane precursor are provided in Table 1 to confirm their identification.

TABLE 1

Organoaminodisilanes Having Formula I

| No. | Precursor Name | MW | Structure | MS Peaks |
|---|---|---|---|---|
| 1 | Di-iso-butylaminodisilane | 189.44 | (iBu)$_2$N–$SiH_2$–$SiH_3$ | 189, 174, 158, 146, 114, 102, 90, 72, 57 |

TABLE 1-continued
Organoaminodisilanes Having Formula I
| No. | Precursor Name | MW | Structure | MS Peaks |
|---|---|---|---|---|
| 2 | Phenylmethylaminodisilane | 167.36 | 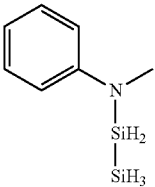 | 167, 136, 119, 106, 93, 78, 58 |
| 3 | 2-(N-disilylmethylamino)pyridine | 168.34 | 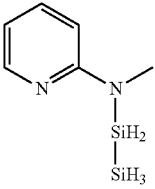 | 167, 137, 121, 108, 93, 78 |
| 4 | Dicyclohexylaminodisilane | 241.52 | 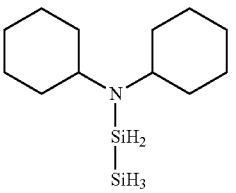 | 241, 210, 198, 138, 103, 55 |
| 5 | Di-sec-butylaminodisilane | 189.44 | 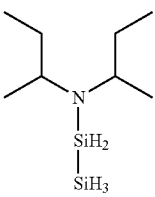 | 189, 176, 160, 128, 100, 72 |
| 6 | Diethylaminodisilane | 133.34 | 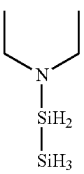 | 133, 118, 102, 86, 72, 58 |
| 7 | Phenylcyclohexylaminodisilane | 235.47 | 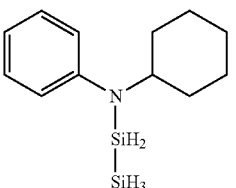 | 235, 204, 192, 178, 160, 150, 120, 107, 93, 77, 55 |
| 8 | Dipropylaminodisilane | 161.39 | 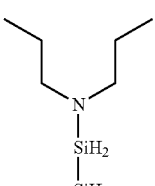 | 161, 132, 100, 88, 72, 58 |

TABLE 1-continued

| | Organoaminodisilanes Having Formula I | | | |
|---|---|---|---|---|
| No. | Precursor Name | MW | Structure | MS Peaks |
| 9 | Dimethylmorpholinodisilane | 175.38 | *morpholine ring with 2,6-dimethyl, N-SiH$_2$-SiH$_3$* | 175, 144, 132, 114, 100, 89, 70, 58 |
| 10 | 2-methylpyrrolidinodisilane | 145.35 | *2-methylpyrrolidine, N-SiH$_2$-SiH$_3$* | 145, 130, 114, 98, 84, 70, 56, 41 |
| 11 | N-ethylisopropylaminodisilane | 147.09 | *iPr(Et)N-SiH$_2$-SiH$_3$* | 147, 132, 114, 100, 86, 72, 58, 40 |
| 12 | N-isopropylmethylaminodisilane | 133.34 | *iPr(Me)N-SiH$_2$-SiH$_3$* | 133, 118, 100, 86, 72, 58, 40 |
| 13 | N-allylphenylaminodisilane | 193.39 | *Ph(allyl)N-SiH$_2$-SiH$_3$* | 193, 178, 162, 148, 133, 119, 93, 77, 51 |
| 14 | 2-methylpiperidinodisilane | 159.38 | *2-methylpiperidine, N-SiH$_2$-SiH$_3$* | 159, 144, 128, 114, 98, 84, 70, 56, 42 |
| 15 | N-phenylethyldisilane | 181.38 | *Ph(Et)N-SiH$_2$-SiH$_3$* | 181, 166, 150, 134, 120, 106, 91, 77, 51 |
| 16 | N-ethylcyclohexyldisilane | 187.43 | *Cy(Et)N-SiH$_2$-SiH$_3$* | 188, 172, 158, 144, 127, 112, 98, 84, 70, 55, 41 |

TABLE 1-continued

Organoaminodisilanes Having Formula I

| No. | Precursor Name | MW | Structure | MS Peaks |
|---|---|---|---|---|
| 17 | 2-methylindolinodisilane | 193.39 | 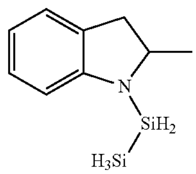 | 193, 178, 160, 146, 132, 118, 91, 70, 53, 39 |
| 18 | Decahydroquinolinodisilane | 199.44 | 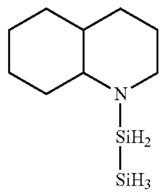 | 198, 182, 168, 152, 138, 124, 111, 96, 81, 67, 44 |
| 19 | 3,5-dimethylpiperidinodisilane | 173.40 | 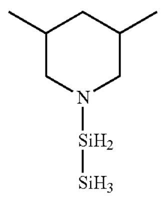 | 173, 158, 142, 126, 112, 90, 70, 56, 41 |
| 20 | N-isopropylcyclohexylaminodisilane | 201.46 | 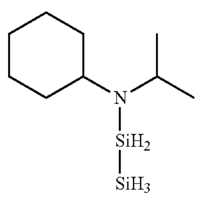 | 201, 186, 171, 154, 141, 126, 112, 98, 84, 70, 55, 41 |
| 21 | 2,5-dimethylpyrrolyldisilane | 155.35 | 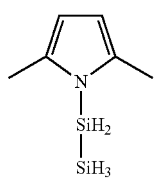 | 155, 139, 123, 109, 94, 79, 65, 39 |
| 22 | tert-butylaminodisilane | 133.34 | 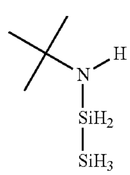 | 133, 118, 102, 86, 74, 57 |
| 23 | iso-propylaminodisilane | 119.31 | 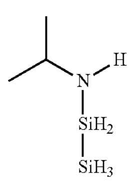 | 119, 104, 88, 72, 59 |
| 24 | Di-iso-butylaminodisilane | 189.44 | 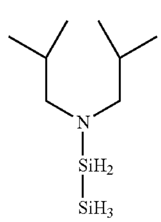 | 189, 174, 158, 146, 114, 102, 90, 72, 57 |

TABLE 1-continued

Organoaminodisilanes Having Formula I

| No. | Precursor Name | MW | Structure | MS Peaks |
|---|---|---|---|---|
| 25 | Phenylisopropylaminodisilane | 195.41 | 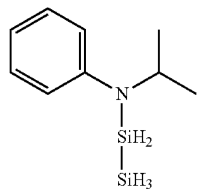 | 195, 180, 164, 148, 134, 120, 93, 77, 59, 43 |
| 26 | N-allylcyclopentylaminodisilane | 185.41 | 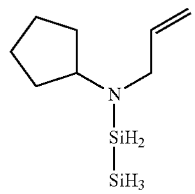 | 185.41 |
| 27 | Dibutylaminodisilane | 189.45 | 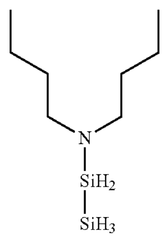 | 189, 156, 146, 130, 114, 104, 86, 74, 58 |
| 28 | Diphenylaminodisilane | 229.43 | 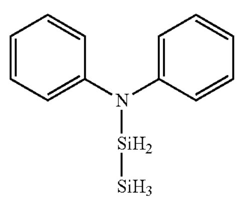 | 229, 214, 198, 181, 167, 143, 120, 105, 93, 77, 66, 51 |
| 29 | 7-Azaindolyldisilane | 178.34 | 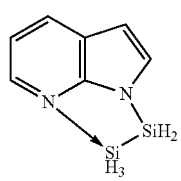 | 177, 161, 145, 130, 118, 102, 91, 78, 70, 54 |
| 30 | N-methylcyclohexylaminodisilane | 173.40 | 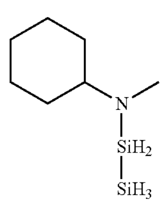 | 173, 158, 142, 130, 117, 98, 85, 70, 55 |
| 31 | 2,6-dimethylpiperidinodisilane | 173.40 | 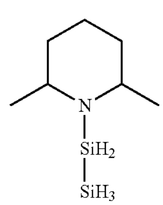 | 173, 158, 142, 126, 112, 98, 87, 72, 55 |

TABLE 1-continued

Organoaminodisilanes Having Formula I

| No. | Precursor Name | MW | Structure | MS Peaks |
|-----|---------------|-----|-----------|----------|
| 32 | 2-ethyl-6-methylanilinodisilane | 195.41 | 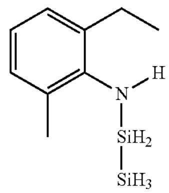 | 195, 180, 162, 148, 134, 120, 105, 91, 77 |
| 33 | N,N,N'-trimethyl-N'-disilylethelenediamine | 162.38 | 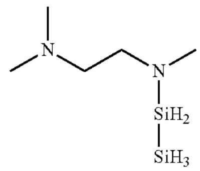 | 161, 146, 131, 114, 104, 86, 72, 58 |
| 34 | 1,1-(N,N'-di-tert-butylethylenediamino)disilane | 230.50 | 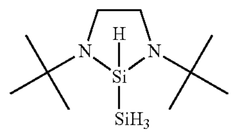 | 230, 215, 199, 185, 173, 100, 86, 57 |

Example 2

Thermal Stability of Di-iso-propylaminodisilane

Approximately 2.0 ml samples of diisopropylaminodisilane (DIPADS) were loaded into 4 stainless steel tubes under dry, inert conditions. The tubes were capped and placed into a lab oven and heated at 80° C. for 4 days. The 4 heated samples were analyzed by GC to determine the extent of degradation relative to the unheated control sample. The samples had an average purity of 99.15% after heating, showing an average degradation of 0.09% relative to the initial purity of 99.24% and demonstrating that DIPADS is suitable precursor for depositing silicon-containing film because of its excellent thermal stability. It is expected that both di-sec-butylaminodisilane and 2,6-dimethylpiperidinodisilane would have similar thermal stability as they have same chemical environments around both silicon atoms as DIPAS.

Comparative Example 2

Thermal Stability of Diethylaminodisilane (DEADS)

Approximately 2 ml of diethylaminodisilane (DEADS) was heated in duplicate sealed stainless steel tubes at 80° C. for 3 days. GC analysis of samples before and after heating showed an average purity drop of 4.4%. Bis(diethylamino)disilane (bis-DEADS) grew in by 3.0% as a result of heating. Disilane was also detected via GC-MS. The observed degradation is consistent with what is reported by Abedini et. al. (Inorg. Chem. Vol 2, 608 (1963)) for dimethylaminodisilane (DMADS) as shown below:

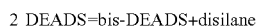

2 DEADS=bis-DEADS+disilane

This seems to suggest both DEADS and DMADS may not be suitable as a precursor for depositing silicon-containing films due to their instability.

Example 3

Cyclic Chemical Vapor Deposition of Amorphous Silicon Films Using Organoaminodisilane Amorphous silicon film was deposited using organoaminodisilane such as diisopropylaminodisilane (DIPADS) and phenylmethylaminodisilane (PMADS) on borosilicate glass and 100 nm Si oxides on Si substrates in cyclic CVD mode at a temperature ranging from 300-400° C. The deposition process was comprised of the following steps a. through c. shown in Table 2 and repeated 1000 times:

TABLE 2

Deposition Parameters Using DIPADS or PMADS

| Step a | 6 sec. (s) | Evacuate reactor | <100 mT |
| Step b | 1 s | Dose organoaminodisilane precursor | Reactor pressure typically <2 Torr |
| Step c | 6 s | Purge reactor with nitrogen | Flow 1.5 slpm $N_2$ |

Although the example uses cyclic CVD deposition, one skilled in the art could transfer the process to conventional thermal CVD process which precursor flow continuously. The deposition rate is reported as film thickness (in Å) as function of silicon precursor flow (in second). Process parameters and resulting films properties are tabulated in Table 3.

TABLE 3

Film Properties of Amorphous Silicon Film Using DIPADS or PMADS

| Wafer temperature (Celcius) | Precursor | Deposition Rate (Å/s) | Ref. Index |
|---|---|---|---|
| 300 | DIPADS | No deposition | N/A |
| 400 | DIPADS | 0.2 | 3.55 |
| 400 | PMADS | 0.1 | N/A |

Figure 2:
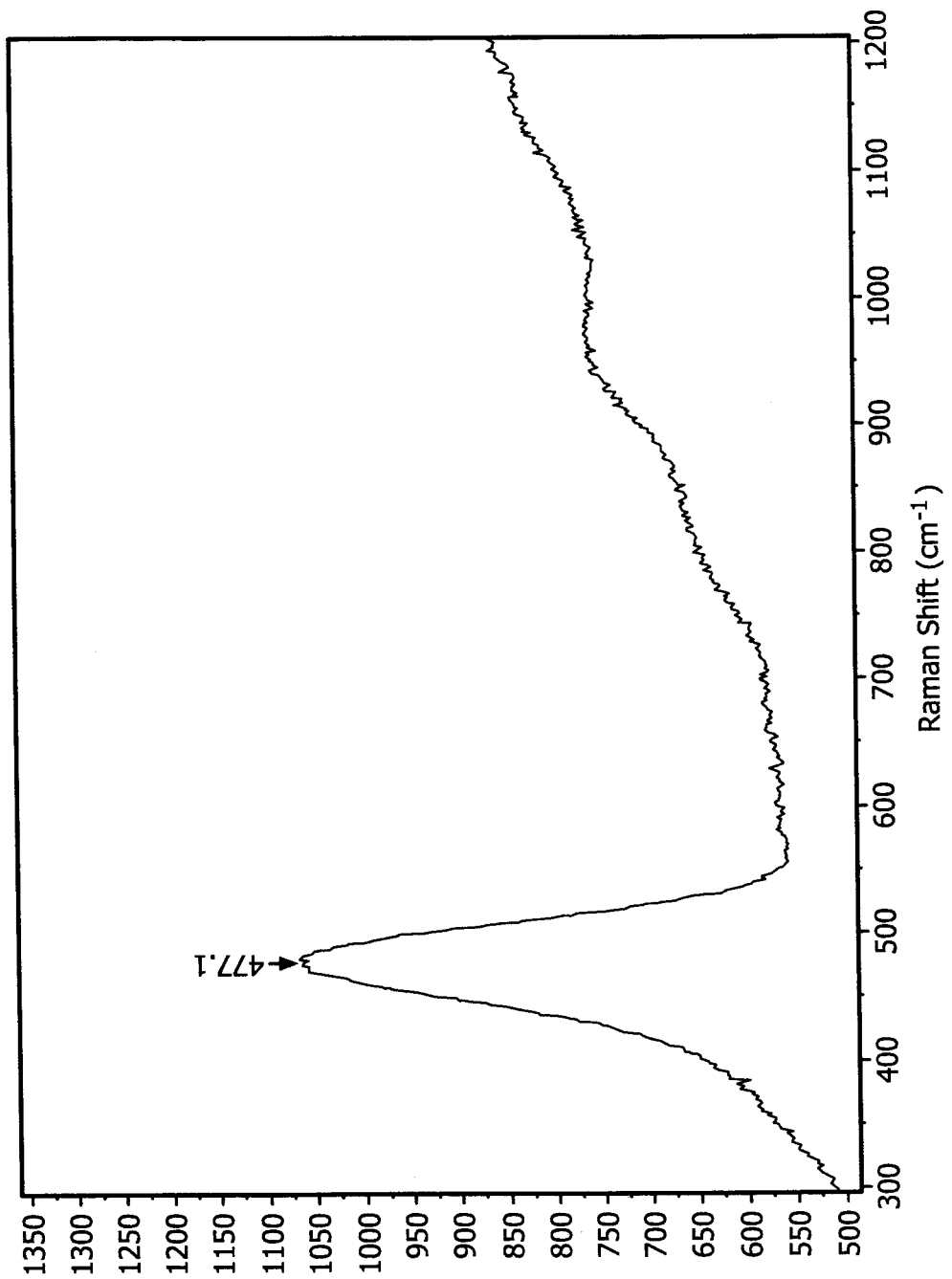
FIG. 2 shows Raman spectrum of amorphous Si film deposited on borosilicate glass described in working example 3 using PMADS.

The films deposited at 400° C. using DIPADS was analyzed using Raman spectroscopy. The film has Raman scattering at 477 cm$^{-1}$ which is provided in FIG. 2 and confirms an amorphous silicon structure.

Example 4

Atomic Layer Deposition of Silicon Oxide Films Using Organoaminodisilane

Atomic layer deposition of silicon oxide films were conducted using di-iso-propylaminodisilane (DIPADS). The depositions were performed on a laboratory scale ALD processing tool. The organoaminodisilane precursor was delivered to the chamber by vapor draw at 55° C. source temperature. All gases (purge, oxygen-containing source and reactant gas) and precursor lines are heated accordingly to ensure precursor flows without any condensation. Gases and precursor flow rates were controlled with ALD diaphragm valves with high speed actuation. The substrates used in the deposition were 12 inch long silicon strips. A thermocouple attached on the sample holder to confirm substrate temperature. Depositions were performed using ozone as the oxygen-containing source gas. The deposition parameters are provided in Table 4.

TABLE 4

Deposition Parameters for Atomic Layer Deposition of Silicon Oxide Films with Ozone Using DIPADS

| Step a | 6 s | Evacuate reactor | <100 mT |
|---|---|---|---|
| Step b | Variable | Dose organoaminodisilane precursor | Reactor pressure typically <2 Torr |
| Step c | 6 s | Purge reactor with nitrogen | Flow 1.5 slpm N$_2$ |
| Step d | 6 s | Evacuate reactor | <100 mT |
| Step e | 4 s | Dose Ozone, 16-20% wt | |
| Step f | 6 s | Purge reactor with nitrogen | Flow 1.5 slpm N$_2$ |

The steps a. through f. in Table 4 are repeated until desired thickness is reached. Thickness and refractive indices of the films were measured using a FilmTek 2000SE ellipsometer by fitting the reflection data from the film to a pre-set physical model (e.g., the Lorentz Oscillator model). The % thickness non-uniformity was calculated from 6-point measurements using the following equation: % non-uniformity= ((max−min)/(2*mean)). Film density was characterized with X-ray reflectometry (XRR). X-ray Photoelectron Spectroscopy (XPS) is used to determine film composition. Film density is characterized using X-ray Reflectometry (XRR). Table 5 summarizes resulting silicon oxide film properties and the film composition and density are provided in Table 6.

TABLE 5

Film properties of Silicon Oxide Deposited from DIPADS and Ozone Process

| Deposition Temperature (° C.) | Precursor Pulse (s) | # of cycles | Deposition Rate (Å/cycle) | Non-uniformity (%) | Ref. Index |
|---|---|---|---|---|---|
| 100 | 1 | 500 | 3.0 | 0.7 | 1.46 |
| 300 | 1 | 350 | 2.8 | 1.0 | 1.44 |

TABLE 6

Composition and Density of Deposited Silicon Oxide Films Using DIPADS

| Deposition Temperature (° C.) | Density (g/cc) | % Si | % O | % C | % N |
|---|---|---|---|---|---|
| 100 | 2.1 | 35.6 | 64.4 | ND | ND |
| 300 | 2.1 | 36.3 | 63.7 | ND | ND |

All deposited films had a refractive index that fell in the range from 1.44 to 1.46, which is a typical refractive index for silicon oxide. Table 6 shows that the carbon and nitrogen contents are below XPS detection limit (<0.1%) for all films. In addition, DIPADS shows significant deposition rate at low temperature (100° C.) which is much better than halogenated disilane precursor such as Si$_2$Cl$_6$ because halogenated precursors are typically not very reactive to ozone or oxygen and require high temperature (>400° C.) for depositing silicon oxide films when ozone is employed as oxygen-containing source. Typical halogenated precursors requires water with catalyst such as pyridine, therefore, they are susceptible to particles formation especially at low temperature.

Figure 3:
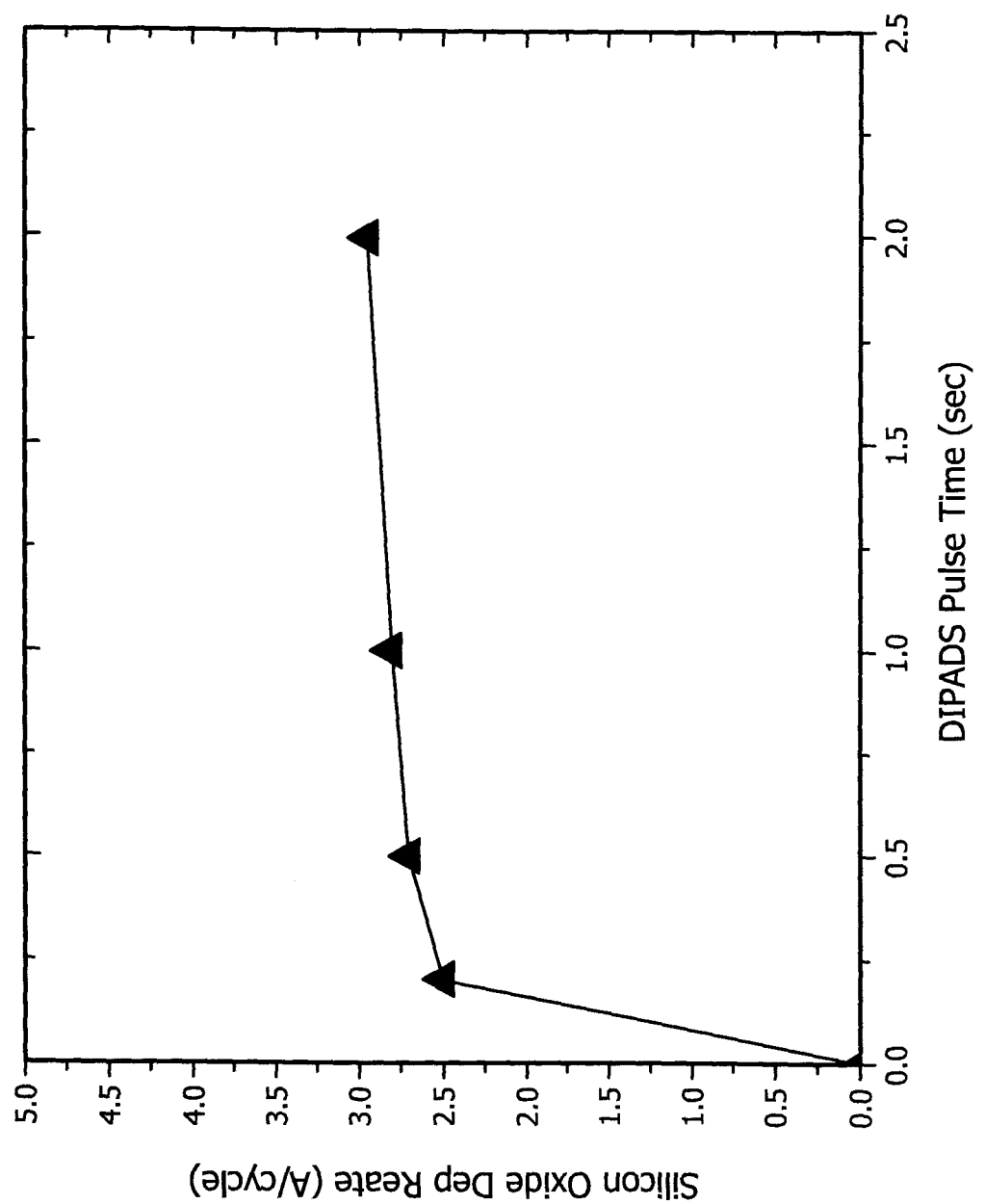
FIG. 3 shows the relationship between deposition rate and pulse time of DIPADS for forming silicon oxide films using DIPADS and ozone at a temperature of 300° C.

FIG. 3 shows the relationship between deposition rate and pulse time of DIPADS for forming a silicon oxide film using DIPADS and ozone at a temperature of 300° C., demonstrating self-limiting behavior of DIPADS and confirming that DIPADS is a suitable precursor for ALD of silicon oxide.

Figure 4:
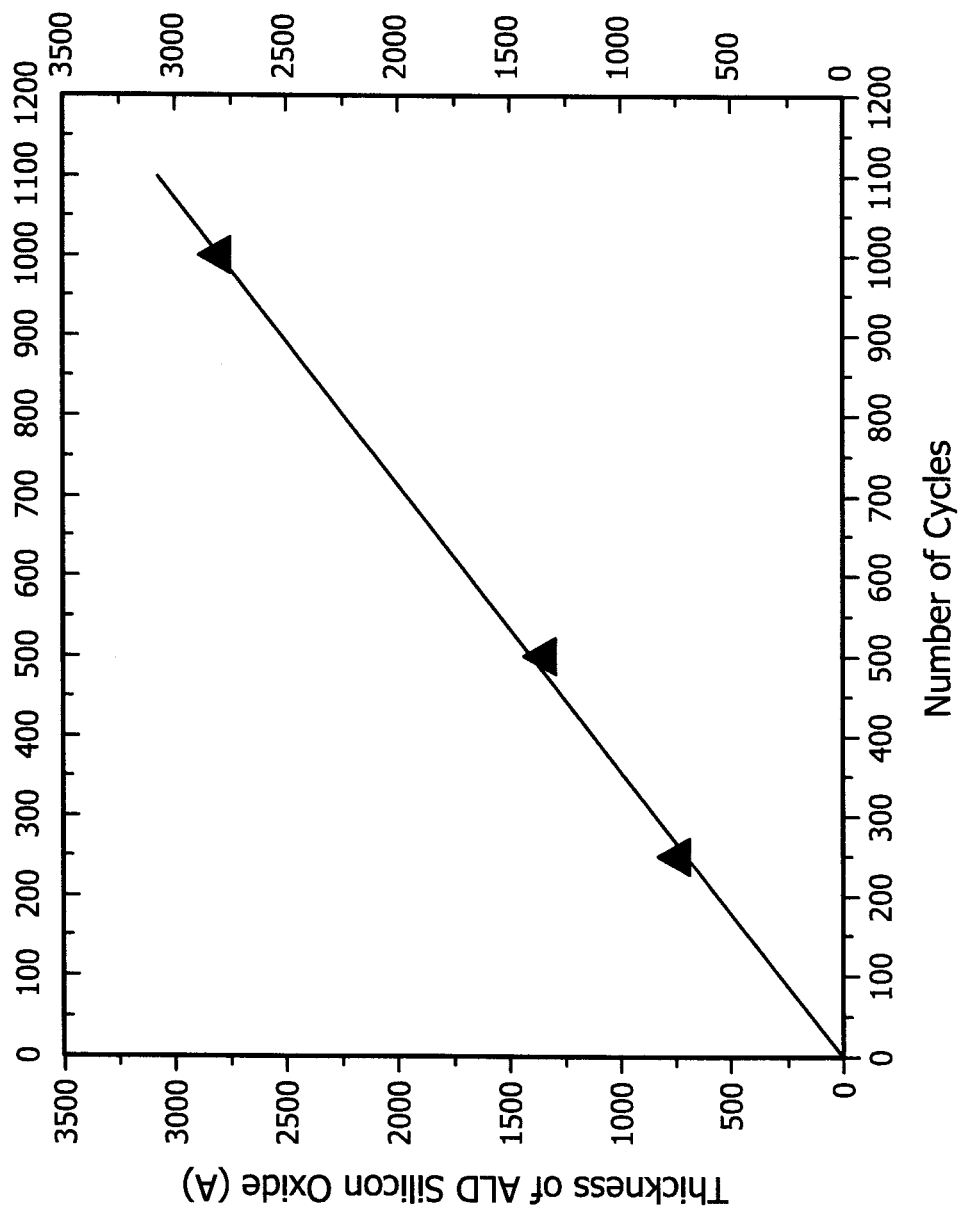
FIG. 4 shows the relationship between thicknesses and the number of cycles for silicon oxide films using DIPADS and ozone at a temperature of 300° C.

FIG. 4 shows the relationship between thicknesses and the number of cycles for forming a silicon oxide film using DIPADS and ozone at a temperature of 300° C., demonstrating good linearity and further confirming DIPADS is a suitable precursor for ALD of silicon oxide.

Example 5

Plasma Enhanced Atomic Layer Deposition of Silicon Oxide Films Using Organoaminodisilane ALD deposition of silicon oxide was conducted from DIPADS and oxygen plasma process using ASM Stellar 3000 production tool on 300 mm Si wafers. Precursor is delivered using Ar carrier gas at room temperature. Oxygen is flowing continuously during process to reduce deposition time. Deposition temperature is set to 30° C. and 100° C. Precursor lines were heated to prevent precursor condensation. Chamber pressure is fixed to 3 Torr during the depositions. The deposition steps and parameters are provided in Table 7.

TABLE 7

Deposition Parameters for Plasma Enhanced Atomic Layer Deposition of Silicon Oxide Films with Oxygen Plasma Using DIPADS

| Step a | 60 s | Evacuate reactor | <100 mTorr |
|---|---|---|---|
| Step b | 60 s | Flow Argon to stabilize reactor pressure | Ar gas flow = 800 sccm Reactor pressure = 3 Torr |
| Step c | 1 s | Dose Organoaminodisilane, Argon and Oxygen | Ar carrier gas flow = 200 sccm Ar gas flow = 800 sccm O$_2$ flow = 100 sccm |

TABLE 7-continued

Deposition Parameters for Plasma Enhanced Atomic Layer
Deposition of Silicon Oxide Films with Oxygen Plasma Using DIPADS

| Step d | 2 s | Remove Organoaminodisilane from reactor using Ar and O₂ gases | Ar gas flow = 800 sccm O₂ flow = 100 sccm |
|---|---|---|---|
| Step e | 2 s | Turn on RF plasma | Plasma power = 200 W |

Steps c to e are repeated for 500 cycles to get a desired thickness of film. Thickness and refractive indices of the deposited films were measured using a FilmTek 2000SE ellipsometer by fitting the reflection data from the film to a pre-set physical model (e.g., the Lorentz Oscillator model). The % thickness non-uniformity was calculated from 9-point measurements using the following equation: % non-uniformity=((max−min)/(2*mean)). Table 8 provides the resulting silicon oxide films properties.

TABLE 8

Film Properties of Silicon Oxide Deposited From DIPADS and Oxygen using Plasma Enhanced Atomic Layer Deposition

| Wafer temperature (Celcius) | Deposition Rate (Å/cycle) | Non-uniformity (%) | Ref. Index | Density (g/cc) | % Si | % O | % C | % N |
|---|---|---|---|---|---|---|---|---|
| 30 | 3.1 | 0.3 | 1.46 | N/A | N/A | N/A | N/A | N/A |
| 100 | 2.9 | 1.3 | 1.46 | 2.1 | 35.1 | 64.9 | ND | ND |

DIPADS deposits high quality silicon oxide films as indicated by a refractive index ranging from 1.45-1.46. Table 8 shows no carbon or nitrogen was detected by XPS. Film density is 2.1 g/cc as determined by XRR. The results in Table 8 indicates that DIPADS shows good deposition rates at even lower temperature such as 30° C. which is superior to halogenated disilane precursor such as $Si_2Cl_6$. It is believed that the good deposition rate is due to the high chemical reactivity of organoaminodisilanes described in this invention.

Example 6

Plasma Enhanced Atomic Layer Deposition of Silicon Nitride or Carbonitride Films Using DIPADS Organoaminodisilane ALD deposition of silicon containing film deposited from DIPADS and nitrogen-hydrogen plasma process using ASM Stellar 3000 production tool on 300 mm Si wafers was conducted. Precursor was delivered using Ar carrier gas at room temperature. Deposition temperature was set to 300° C. Precursor lines were heated accordingly to prevent precursor condensation. Chamber pressure was fixed to 3 Torr during depositions. Deposition steps and parameters are provided in Table 9.

TABLE 9

Deposition Parameters for DIPADS using $N_2/H_2$ Plasma

| Step a | 300 sec | Evacuate reactor | <100 mTorr |
|---|---|---|---|
| Step b | 60 sec | Flow Argon stabilizing reactor pressure | Ar gas flow = 1200 sccm Reactor pressure = 3 Torr |
| Step c | 1 sec | Dose Organoaminodisilane, nitrogen and hydrogen gas | Ar carrier gas flow = 400 sccm Ar process gas flow = 1200 sccm N₂ flow = H₂ flow = 250 sccm |
| Step d | 4 sec | Remove silicon precursor from reactor using Ar, H₂ and N₂ gases | Ar process gas flow = 1200 sccm N₂ flow = H₂ flow = 250 sccm |
| Step e | 2 sec | Turn on RF plasma | Plasma power = 500 W |

Steps c to e are repeated for 500 cycles to get a desired film thickness. The thickness non-uniformity was calculated from 9-point measurements using the following equation: % non-uniformity=((max−min)/(2*mean)). X-ray Photoelectron Spectroscopy (XPS) was used to determine film composition while X-ray Reflectometry (XRR) for density measurements. Table 10 summarizes the resulting film properties.

TABLE 10

Film Properties of SiCxNy Deposited from DIPADS and $N_2/H_2$ Plasma Process at 300° C.

| Precursor Purge (sec) | Deposition Rate (Å/cycle) | Non-uniformity (%) | Ref. Index | Density (g/cc) | % O | % N | % C | % Si |
|---|---|---|---|---|---|---|---|---|
| 4 | 0.3 | 2.4 | 1.76 | 2.1 | 3.5 | 45.5 | 12.1 | 38.9 |
| 1 | 0.8 | 6.1 | 1.76 | 2.0 | 2.6 | 41.2 | 14.2 | 41.6 |

Example 7

Cyclic Chemical Vapor Deposition of Silicon Oxide Films Using Organoaminodisilane A silicon containing film was deposited in cyclic chemical vapor deposition mode using PMADS and ozone ($O_3$). The deposition steps are as shown in Table 11 below and the deposition temperature was 300° C.

TABLE 11

Deposition Parameter of Silicon Oxide Deposited from PMADS and Ozone Using CCVD Process

| Step a | 6 s | Evacuate reactor | <100 mT |
|---|---|---|---|
| Step b | 6 s | Dose Organoaminodisilane | Reactor pressure typically <2 Torr |
| Step c | 4 s | Dose $O_3$ (15-20% wt) | |

Steps b to c are repeated for 500 cycles to get a desired film thickness. The deposited film had a RI of 1.48 and a uniformity of 2.3%; the deposition rate of 3.7 Å/cycle. Dosing oxidant without purging after the organoaminodisilane delivery step enhanced the deposition rate but still provided good uniformity, further confirming the high surface chemical reactivity of organoaminodisilane described in this invention.

Prophetic Example 8

PEALD Silicon Carbonitride Film Using di-iso-propylaminodisilane (DIPADS) and Ar Plasma The silicon wafer is loaded into Stellar 3000 PEALD reactor and heated to 300° C. with chamber pressure of about 2-5 Torr. The deposition process is performed in a manner similar to the steps described in Example 6, Table 9 except that only Ar plasma is used in Steps d to e and repeated 1000 times.

Prophetic Example 9

PEALD Amorphous Silicon Film Using di-iso-propylaminodisilane (DIPADS) and Hydrogen/Argon Plasma The silicon wafer is loaded into Stellar 3000 PEALD reactor and heated to 300° C. with chamber pressure of about 2-5 Torr. The deposition process is performed in a manner similar to the steps described in Example 6, Table 9 except that only a plasma comprising hydrogen and argon plasma is used in Steps d to e and repeated 1000 times.

Prophetic Example 10

PEALD Silicon Carbonitride Film Using di-sec-butylaminodisilane (DSBADS) and Ar Plasma The silicon wafer is loaded into Stellar 3000 PEALD reactor and heated to 300° C. with chamber pressure of about 2-5 Torr. The deposition process is performed in a manner similar to the steps described in Example 6, Table 9 except that only Ar plasma is used in Steps d to e and repeated 1000 times.

Prophetic Example 11

PEALD Amorphous Silicon Film Using di-sec-butylaminodisilane (DSBADS) and Hydrogen/Argon Plasma The silicon wafer is loaded into Stellar 3000 PEALD reactor and heated to 300° C. with chamber pressure of about 2-5 Torr. The deposition process is performed in a manner similar to the steps described in Example 6, Table 9 except that only a plasma comprising hydrogen and argon plasma is used in Steps d to e and repeated 1000 times.

The invention claimed is:

1. A composition comprising at least one organoaminodisilane selected from the group consisting of di-iso-probylaminodisilane, di-sec-butylaminodisilane, di-tert-butylaminodisilane, 2,6-dimethylpiperidinodisilane, 2,2,6,6-tetramethylpiperidinodisilane, cyclohexyl-iso-probylaminodisilane, phenylmethylaminodisilane, phenylethylaminodisilane, di-cyclohexylaminodisilane, trans-decahydroguinolinyldisilane, 1,1-bis(t-butylamino)disilane, 1,1-bis(tert-pentylamino)disilane, 1,1-bis(iso-propylamino)disilane, 1,1-bis(iso-propylmethlamino)disilane, 1,1-dipiperidinodisilane, 1,1-dipyrrolidinodisilane, 1,1-di(2,6-dimethylpiperidino)disilane, and 1,1-bis(di-sec-butylamino)disilane;

wherein the composition is substantially free of halide ions.

2. The composition of claim 1 wherein the organoaminodisilane is selected from the group consisting of di-iso-propylaminodisilane, di-sec-butylaminodisilane, 2,6-dimethylpiperidinodisilane, phenylmethylaminodisilane, and phenylethylaminodisilane.

3. The composition of claim 2 wherein the organoaminodisilane comprises di-iso-propylaminodisilane.

4. The composition of claim 2 wherein the organoaminodisilane comprises di-sec-butylaminodisilane.

5. The composition of claim 2 wherein the organoaminodisilane comprises 2,6-dimethylpiperidinodisilane.

6. The composition of claim 2 wherein the organoaminodisilane comprises phenylethylaminodisilane.

7. The composition of claim 1 wherein the halide ions are chloride ions.

8. The composition of claim 7, which comprises less than 5 ppm of chloride ions.

9. The composition of claim 7, which comprises less than 3 ppm of chloride ions.

10. The composition of claim 7, which comprises less than 1 ppm of chloride ions.

11. A composition comprising:
   (a) at least one organoaminodisilane selected from the group consisting of di-iso-propylaminodisilane, di-sec-butylaminodisilane, di-tert-butylaminodisilane, 2,6-dimethylpiperidinodisilane, 2,2,6,6-tetramethylpiperidinodisilane, cyclohexvl-iso-propylaminodisilane, phenylmethylaminodisilane, phenylethylaminodisilane, di-cyclohexylaminodisilane, trans-decahydroguinolinyldisilane, 1,1-(N,N'-di-tert-butylethylenediamino)disilane, 1,1-(N,N'-di-iso-propylethylenediamino)disilane, 1,1-bis(t-butylamino)disilane, 1,1-bis(tert-pentylamino)disilane, 1,1-bis(iso-propylamino)disilane, 1,1-bis(iso-propylmethlamino)disilane, 1,1-dipiperidinodisilane, 1,1-dipyrrolidinodisilane, 1,1-bis(diethylamino)disilane, 1,1-bis(di-iso-propylamino)disilane, 1,1-di(2,6-dimethylpiperidino)disilane, and 1,1-bis(di-sec-butylamino)disilane; and (b) a solvent, wherein the solvent has a boiling point, wherein the difference between the boiling point of the solvent and that of the at least one organoaminodisilane is 40° C. or less, and wherein the composition is substantially free of halide ions.

12. The composition of claim 11 wherein the organoaminodisilane comprises at least one of di-iso-propylaminodisilane, di-sec-butylaminodisilane, 2,6-dimethylpiperidinodisilane,-phenylmethylaminodisilane, and phenylethylaminodisilane.

13. The composition of claim 11 wherein the solvent comprises at least one selected from the group consisting of ether, tertiary amine, alkyl hydrocarbon, aromatic hydrocarbon, and tertiary aminoether.

14. The composition of claim 11, wherein the halide ions are chloride ions.

15. The composition of claim 14, which comprises less than 5 ppm of chloride ions.

16. The composition of claim 14, which comprises less than 3 ppm of chloride ions.

17. The composition of claim 14, which comprises less than 1 ppm of chloride ions.

18. The composition of claim 1 further comprising a nitrogen-containing source wherein the at least one organoaminodisilane and the nitrogen-containing source can react to form a silicon containing film.

19. The composition of claim 18 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

20. The composition of claim 18 wherein the silicon-containing film is selected from the group consisting of silicon nitride and silicon carbonitride.

* * * * *

UNITED STATES PATENT AND TRADEMARK OFFICE
CERTIFICATE OF CORRECTION

PATENT NO. : 9,627,193 B2
APPLICATION NO. : 14/511719
DATED : April 18, 2017
INVENTOR(S) : Steven Gerard Mayorga et al.

It is certified that error appears in the above-identified patent and that said Letters Patent is hereby corrected as shown below:

In the Claims

Column 46, Claim 1, Line 16:
Delete the compound "di-iso-probylaminodisilane", and insert the compound
-- di-iso-propylaminodisilane --.

Signed and Sealed this
Twenty-fourth Day of March, 2020

Andrei Iancu
*Director of the United States Patent and Trademark Office*